US012716093B2

(12) United States Patent
Lackey et al.

(10) Patent No.: US 12,716,093 B2
(45) Date of Patent: Aug. 25, 2026

(54) METHODS AND COMPOSITIONS RELATING TO CONTINUOUS SEQUENCING

(71) Applicant: Twist Bioscience Corporation, South San Francisco, CA (US)

(72) Inventors: Jeremy Lackey, Foster City, CA (US); William Banyai, San Francisco, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 931 days.

(21) Appl. No.: 18/047,228

(22) Filed: Oct. 17, 2022

(65) Prior Publication Data

US 2023/0127969 A1 Apr. 27, 2023

Related U.S. Application Data

(60) Provisional application No. 63/256,866, filed on Oct. 18, 2021.

(51) Int. Cl.
*C12Q 1/68* (2018.01)
*C12Q 1/6869* (2018.01)
*C40B 40/06* (2006.01)

(52) U.S. Cl.
CPC ............ *C12Q 1/6869* (2013.01); *C40B 40/06* (2013.01)

(58) Field of Classification Search
CPC .............................. C12Q 1/6869; C40B 40/06
See application file for complete search history.

(56) References Cited

U.S. PATENT DOCUMENTS

| | | | |
|---|---|---|---|
| 6,296,810 | B1 | 10/2001 | Ulmer |
| 2017/0369941 | A1 | 12/2017 | Rudi et al. |
| 2019/0040457 | A1 | 2/2019 | Hall |
| 2019/0345544 | A1 | 11/2019 | Middleton et al. |
| 2019/0360039 | A1 | 11/2019 | Bashkirov et al. |
| 2020/0032317 | A1 | 1/2020 | Rohrman et al. |
| 2020/0131486 | A1 | 4/2020 | Iyidogan et al. |
| 2020/0332333 | A1 | 10/2020 | Chen et al. |
| 2021/0269876 | A1 | 9/2021 | Pham et al. |
| 2021/0301336 | A1 | 9/2021 | Bashkirov et al. |

FOREIGN PATENT DOCUMENTS

| | | | |
|---|---|---|---|
| WO | 2012129242 | A2 | 9/2012 |
| WO | 2016026924 | A1 | 2/2016 |

OTHER PUBLICATIONS

International Search Report and Written Opinion for International Application No. PCT/US2022/046906, mailed on Mar. 2, 2023, 15 pages.

*Primary Examiner* — Jezia Riley
(74) *Attorney, Agent, or Firm* — Bookoff McAndrews, PLLC

(57) ABSTRACT

Provided herein are compositions, devices, systems and methods for polynucleotide sequencing. Further provided are devices comprising surfaces for continuous sequencing. The compositions, devices, systems and methods described herein provide improved storage, density, and retrieval of biomolecule-based information.

19 Claims, 10 Drawing Sheets

METHODS AND COMPOSITIONS RELATING TO CONTINUOUS SEQUENCING

CROSS-REFERENCE

This application claims the benefit of U.S. provisional patent application No. 63/256,866 filed on Oct. 18, 2021, which is incorporated by reference in its entirety.

BACKGROUND

Biomolecules (e.g., nucleic acids) have applications in research, medicine, and information storage. However, there is a need for high-density, scalable, automated, highly accurate and highly efficient systems for sequencing biomolecules.

BRIEF SUMMARY

Provided herein are methods for polynucleotide sequencing comprising: a) contacting a plurality of polynucleotides with at least one primer and at least one polymerase to form a plurality of ternary complexes; b) detecting one or more bases of the polynucleotides, wherein detection occurs when the plurality of ternary complexes are bound to a surface; c) removing the ternary complexes from the surface; and d) repeating steps a-c to sequence the polynucleotides. Further provided herein are methods wherein step c) comprises washing the surface. Further provided herein are methods wherein washing comprises contacting the surface with one or more of a solvent, heat, small molecule, nucleic acid, or protein. Further provided herein are methods wherein the small molecule comprises a first moiety configured for conjugation to a second moiety. Further provided herein are methods wherein the conjugation comprises nucleophile/carbonyl; an azide/phosphine; 1,4 Michael addition, 1,3-dipolar cycloaddition, inverse electron demand cycloaddition; olefin metathesis; or cross-coupling reaction. Further provided herein are methods wherein the small molecule comprises biotin, alkyne, azide, tetrazine, alkene, alkyne, carbonyl, Michael acceptor/donor, or antigen. Further provided herein are methods wherein the solvent comprises an organic solvent. Further provided herein are methods wherein the organic solvent comprises MeCN, methanol, ethanol, 2-propanol, acetone, DMF, formamide, THF, or DMSO. Further provided herein are methods wherein the organic solvent is heated. Further provided herein are methods wherein the protein comprises a proteinase or nuclease. Further provided herein are methods wherein the proteinase comprises an aminopeptidase. Further provided herein are methods wherein the aminopeptidase comprises proteinase K, N-terminal aminopeptidases, C-terminal aminopeptidases, chymotrypsin, trypsin, pepsin, or LysC. Further provided herein are methods wherein the protein comprises streptavidin. Further provided herein are methods wherein the polymerase comprises a Phi29 polymerase or variant thereof. Further provided herein are methods wherein the polymerase is bound to the surface in step a). Further provided herein are methods wherein the polymerase is not bound to the surface in step a). Further provided herein are methods wherein the plurality of polynucleotides comprises at least 100,000 unique polynucleotides. Further provided herein are methods wherein the plurality of polynucleotides are 50-30,000 bases in length. Further provided herein are methods wherein detecting comprises identification of bases using unique wavelengths, fluorescence lifetime, or changes in current or voltage. Further provided herein are methods wherein detecting comprises one or more of sequencing by synthesis and nanopore detection. Further provided herein are methods wherein detecting comprises FRET. Further provided herein are methods wherein detecting comprises contacting the ternary complexes with at least one nucleotide. Further provided herein are methods wherein the nucleotide comprises a label. Further provided herein are methods wherein the label comprises a luminescent label. Further provided herein are methods wherein the luminescent label is a dye. Further provided herein are methods wherein the polymerase is attached to a quantum dot. Further provided herein are methods wherein the plurality of polynucleotides are bound to the surface in step a). Further provided herein are methods wherein detecting comprises excitation with electromagnetic energy. Further provided herein are methods wherein detecting comprises excitation with a laser. Further provided herein are methods wherein the laser is pulsed. Further provided herein are methods wherein the plurality of polynucleotides comprise hairpin adapters. Further provided herein are methods wherein the plurality of polynucleotides are circular. Further provided herein are methods wherein steps a-c are repeated at least three times. Further provided herein are methods wherein steps a-c are repeated at least 20 times. Further provided herein are methods wherein steps a-c occur in no more than 10 min. Further provided herein are methods wherein step c occurs in no more than 5 min.

Provided herein are methods for polynucleotide sequencing comprising: a) sequencing a plurality of polynucleotides on a surface, wherein the surface comprises a plurality of loci for single-molecule sequencing; b) removing the polynucleotides from the surface; and c) repeating steps a-b to sequence the polynucleotides, wherein at least 1 megabyte of sequencing data is acquired in no more than 1 hour from no more than 150,000 loci of the plurality of loci on the surface. Further provided herein are methods wherein at least 1 gigabyte of sequencing data is acquired in no more than 1 hour from no more than 150,000 loci of the plurality of loci on the surface. Further provided herein are methods wherein at least 1 terabyte of sequencing data is acquired in no more than 1 hour from no more than 150,000 loci of the plurality of loci on the surface. Further provided herein are methods wherein 1 megabyte to 1 zettabyte of sequencing data is acquired in no more than 1 hour from no more than 150,000 loci of the plurality of loci on the surface. Further provided herein are methods wherein the plurality of polynucleotides encodes for at least 1 Gb of digital information.

Provided herein are methods encoding an item of digital information comprising: a) providing an item of information as a digital sequence; b) encoding the digital sequence as a nucleic acid sequence; and c) generating the plurality of polynucleotides described herein.

Provided herein are methods for decoding an item of digital information comprising: obtaining nucleic acid sequences of the plurality of polynucleotides using a method described herein; decoding the nucleic acid sequences into one or more digital sequences; and reading an item of digital information using the one or more digital sequences.

Provided herein are devices for nucleic acid sequencing comprising: a solid support, wherein the solid support comprises a surface, and wherein the surface comprises a plurality of loci; a binding moiety covering at least some of the loci, wherein the binding moiety is configured to bind one or more polynucleotides, polymerases, primers, and a complex of any combination thereof, and wherein the surface is reusable; and a detector, wherein the detector is configured to discriminate the identity of one or more bases added by the polymerase. Further provided herein are devices wherein the surface is reusable without removal of the binding moiety. Further provided herein are devices wherein the surface is reusable without chemical modification. Further provided herein are devices wherein the device comprises at least 100,000 loci per $mm^2$. Further provided herein are devices wherein the device comprises at least 1,000,000 loci per $mm^2$. Further provided herein are devices wherein the device comprises 100,000 to 1 billion loci per $mm^2$. Further provided herein are devices wherein primers have a length of 15-50 bases. Further provided herein are devices wherein the surface comprises a plurality of wells or channels. Further provided herein are devices wherein the wells or channels have a longest linear dimension of 10-200 nm. Further provided herein are devices wherein the device further comprises one or more nanopores. Further provided herein are devices wherein the surface is a substantially planer surface. Further provided herein are devices wherein the solid support comprises glass, silicon, or a combination thereof. Further provided herein are devices wherein surface comprises a plurality of polymerases attached thereto. Further provided herein are devices wherein surface comprises a plurality of polynucleotides attached thereto. Further provided herein are devices wherein the surface comprises a complex comprising two or more of polynucleotides, polymerases, or primers. Further provided herein are devices wherein at least 1% of loci comprise a polymerase, polynucleotide, primer, or complex of any combination thereof. Further provided herein are devices wherein at least 30% of loci comprise a polymerase, polynucleotide, primer, or complex of any combination thereof. Further provided herein are devices wherein the complex is attached via covalent binding. Further provided herein are devices wherein the complex is attached via non-covalent binding. Further provided herein are devices wherein the complex is attached via affinity interaction, protein, oligonucleotide, or heat releasable linkage. Further provided herein are devices wherein the affinity interaction comprises Streptavidin-biotin. Further provided herein are devices wherein the affinity interaction comprises anti-body-antigen binding. Further provided herein are devices wherein the affinity interaction comprises protein-protein interactions. Further provided herein are devices further comprising a fluidics interface. Further provided herein are devices further comprising a flow cell. Further provided herein are devices wherein the device comprises at least one detector per loci. Further provided herein are devices wherein the detector comprises a plurality of zero-mode waveguides. Further provided herein are devices wherein the detector is configured to measure visible wavelengths, UV wavelengths, or a combination thereof. Further provided herein are devices wherein the detector is configured to measure fluorescence. Further provided herein are devices wherein the detector is configured to measure changes in voltage or current. Further provided herein are devices further comprising a polynucleotide synthesis device.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
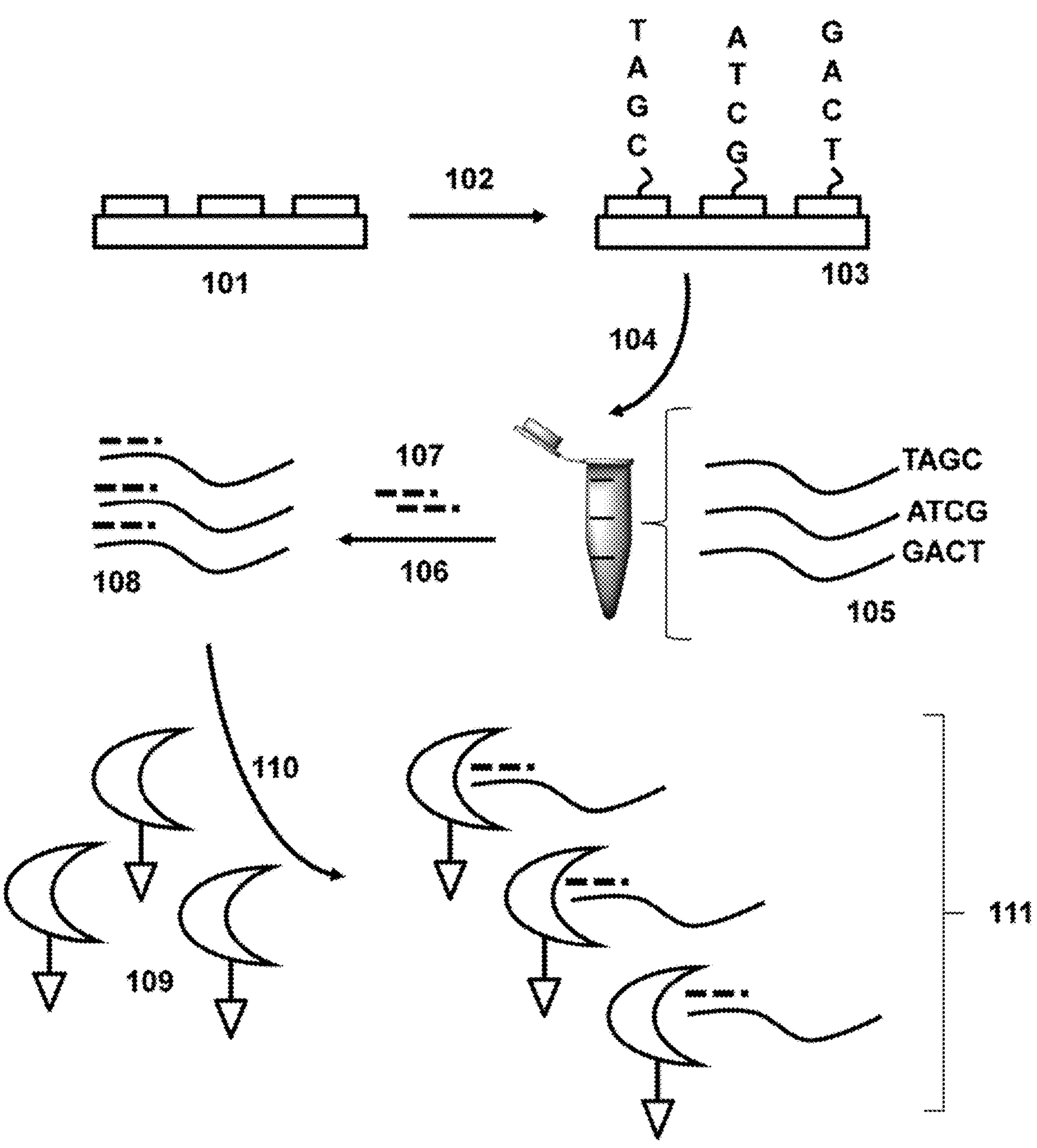
FIG. 1 illustrates a non-limiting example of a scheme for polynucleotides synthesis and preparation prior to sequencing.

There is a need for larger capacity storage systems as the amount of information generated and stored is increasing exponentially. A biomolecule such as a DNA molecule provides a suitable host for information storage in-part due to its stability over time and capacity for four bit information coding, as opposed to traditional binary information coding. Provided herein are devices and methods to increase nucleic acid reading speed and efficiency using continuous workflows. Further provided herein are devices and methods for reusing or recycling surfaces for single molecule sequencing.

DEFINITIONS

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the polynucleotide being known and chosen before the synthesis or assembly of the nucleic acid molecules.

As used herein, the term "symbol," generally refers to a representation of a unit of digital information. Digital information may be divided or translated into one or more symbols. In an example, a symbol may be a bit and the bit may have a numerical value. In some examples, a symbol may have a value of '0' or '1'. In some examples, digital information may be represented as a sequence of symbols or a string of symbols. In some examples, the sequence of symbols or the string of symbols may comprise binary data.

Provided herein are methods and compositions for production and sequencing of synthetic (e.g. de novo synthesized or chemically synthesized) polynucleotides. Polynucleotides may also be referred to as oligonucleotides or oligos. Polynucleotide sequences described herein may be, unless stated otherwise, comprise DNA or RNA.

Continuous Sequencing

Polynucleotides sequenced using the methods described herein encode data that can be interpreted by reading the sequence of synthesized polynucleotides and converting the sequence into code comprising one or more symbols readable by a computer, such as binary code. In some cases, the sequences require assembly, and the assembly step may occur at the nucleic acid sequence stage or at the digital sequence stage. Sequencing in some instances comprises discriminatory identification/detection of individual bases in a sequence. In some instances, sequencing is performed on individual molecules on devices.

Provided herein are sequencing systems that can be integrated into the devices described herein. Various methods of sequencing are well known in the art, and comprise "base calling" where the identity of a base in a sample polynucleotide is identified/sequenced. In some instances, polynucleotides synthesized using the methods, devices, compositions, and systems described herein are sequenced after cleavage from the synthesis surface. In some instances, sequencing occurs during or simultaneously with polynucleotide synthesis, wherein base calling occurs immediately after or before extension of a nucleoside monomer into the growing polynucleotide chain. Methods for base calling include measurement of electrical currents/voltages (e.g., AC or DC), fluorescence, or other measurement generated by polymerase-catalyzed addition (or transient binding) of bases to a template strand. In some instances, synthesis surfaces or sequencing surfaces comprise enzymes, such as polymerases. In some instances, such enzymes are tethered to electrodes or to the synthesis or sequencing surface. In some instances, the synthesis or sequencing surface comprises a plurality of loci (e.g., arrangement spots), or wells (e.g., nanopores). After sequencing, in some instances one or more of polymerases, primers, or sample polynucleotides are removed from the surface of a device, and new components are added to facilitate a second cycle of sequencing using the same device surface. This process in some instances is repeated numerous times to sequence large numbers of sample polynucleotides.

Provided herein are detection systems comprising a device for sequencing stored polynucleotides, either directly on the structure and/or after removal from a structure (e.g., solid support). In some instances, devices comprise one or more of a surface, a fluidics interface, and a detector. In some instances, the signal is indicative of a presence of a polynucleotide. In some instances, the signal is indicative of a sequence of a polynucleotide (e.g., a fluorescent signal). In some instances, a detection system comprises a computer system comprising a polynucleotide sequencing device, a database for storage and retrieval of data relating to polynucleotide sequence, software for converting DNA code of a polynucleotide sequence to one or more symbols, such as binary code, a computer for reading the binary code, or any combination thereof. In some instances, a described herein comprises one or more of a solid support, a binding moiety covering at least some of the loci, and a detector. In some instances, at least some of the loci comprise single sample polynucleotides. In some instances the solid support comprises a surface. In some instances, the surface comprises a plurality of loci. In some instances, the binding moiety is configured to bind one or more polynucleotides, polymerases, primers, and a complex of any combination thereof. In some instances, the detector is configured to discriminate the identity of one or more bases added by the polymerase. In some instances, the surface is reusable.

Devices described herein may comprise one or more detectors. In some instances, a detector comprises an electromagnetic radiation source. In some instances, the electromagnetic radiation source is configured to produce visible, infrared, or UV wavelength light. In some instances, devices comprise one or more zero-mode waveguides. In some instances, devices comprise one or more nanopores.

Devices described herein may comprise structures comprising flexible surfaces. In cases where the structure is a reel-to-reel tape of flexible material, the detection system in some instances comprises a device for holding and advancing the structure through a detection location and a detector disposed proximate the detection location for detecting a signal originating from a section of the tape when the section is at the detection location. In some instances, information encoded within polynucleotides on a continuous tape is read by a computer as the tape is conveyed continuously through a detector operably connected to the computer.

Provided herein are methods for polynucleotide sequencing. In some instances, a method described herein comprises one or more steps of (a) contacting a plurality of polynucleotides with at least one primer and at least one polymerase to form a plurality of ternary complexes; (b) detecting one or more bases of the polynucleotides, wherein detection occurs when the plurality of ternary complexes are bound to a surface; (c) removing the ternary complexes from the surface; and (d) repeating steps a-c to sequence the polynucleotides. In some instances, the method comprises washing the surface. Prior to sequencing, polynucleotides are synthesized and prepared for sequencing, as illustrated, in a non-limiting example, through the scheme illustrated in FIG. 1. The polynucleotides are synthesized on a synthesis surface 101, using methods as described herein. DNA synthesis 102 is performed, resulting in a plurality of polynucleotides on the synthesis surface 103. The synthesized polynucleotides are removed from a surface 104 and collected, for example in a microcentrifuge tube or other suitable medium or container. In some instances, the microcentrifuge tube containing free polynucleotides 105 contains a buffer solution suitable for preserving the polynucleotides. In some cases, the polynucleotides are circular. In some cases, the polynucleotides comprise hairpin adapters. In some instances, the polynucleotides are amplified on the synthesis surface or after being removed from the synthesis chip. Primers 107 and polymerase enzymes 109 are also contacted with the polynucleotides. In some instances, the primers 107 are added in a following step 106 to the polynucleotides, resulting in primer and polynucleotide complexes 108. In some cases, the primers 107 are no more than 10 base pairs, 20 base pairs, 30 base pairs, 40 base pairs, 50 base pairs, or 60 base pairs. In further instances, polymerase enzymes 109 are added in a further step 110 to the microcentrifuge tube, resulting in a plurality of ternary complexes 111. In some examples, the polymerase enzymes 109 comprise a first moiety, which may be a binding moiety. In some examples, the first moiety on the polymerase enzymes 109 comprises biotin. In some examples, the first moiety on the polymerase enzymes 109 comprises a protein chain. In some examples, the first moiety on the polymerase enzymes 109 comprises an oligonucleotide. In some instances, the polymerase enzymes 109 comprise, by way of non-limiting example, bacteriophage phi29 (Φ29) polymerase, genetically modified phi29 (Φ29) DNA polymerase, Therminator DNA polymerase, Klenow Fragment of DNA polymerase I, phage M2 DNA polymerase, phage phiPRD1 DNA polymerase, Bst DNA polymerase, exo(−)Bca DNA polymerase, Bsu DNA polymerase, VentR DNA polymerase (e.g., VentR (exo-) DNA polymerase), Deep Vent DNA polymerase (e.g., Deep Vent (exo-) DNA polymerase), IsoPol DNA polymerase, DNA polymerase I, T5 DNA polymerase, Sequenase, T7 DNA polymerase, T7-Sequenase, T7 gp5 DNA polymerase, PRDI DNA polymerase, or T4 DNA polymerase. In some instances, additional strand displacing nucleic acid polymerases are also compatible with the methods described herein. The ability of a given polymerase to carry out strand displacement replication can be determined, for example, using the polymerase in a strand displacement replication assay. Such assays, in some instances, are performed at a temperature suitable for optimal activity for the enzyme being used, for example, 32° C. for phi29 DNA polymerase, from 46° C. to 64° C. for exo(−) Bst DNA polymerase, or from about 60° C. to 70° C. for an enzyme from a hyperthermophylic organism. In some instances, another useful assay for selecting a polymerase is the primer-block assay. In some instances, the polymerase comprises C1, C2, P4-XL, P5-C3, or P6-C4 (Pacific Biosciences).

Figure 2:
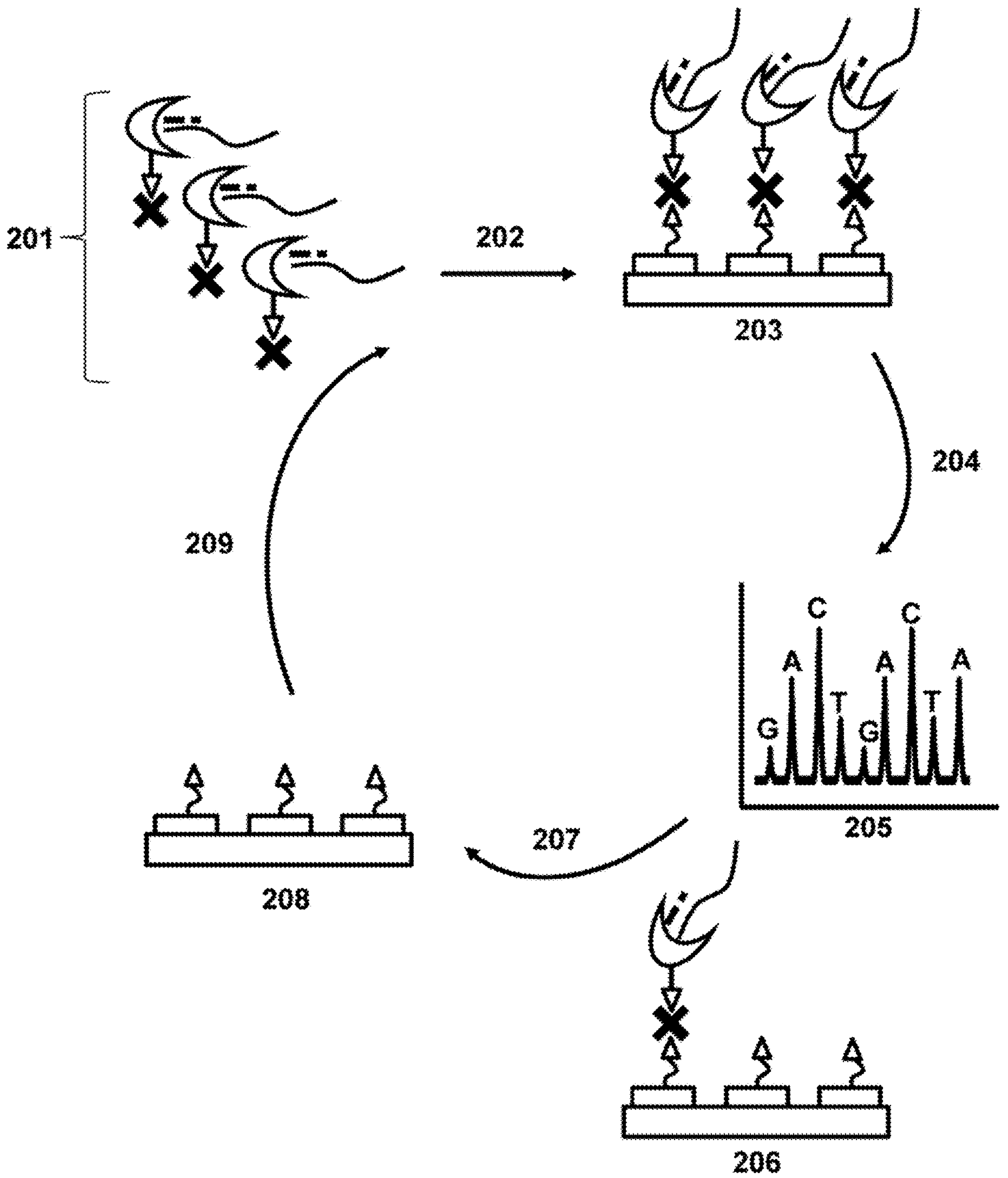
FIG. 2 illustrates a non-limiting example of a scheme for polynucleotide sequencing, in this case with a reusable sequencing chip.

After extraction and/or amplification of polynucleotides from the surface of the structure, suitable sequencing technology may be employed to sequence the polynucleotides. In some cases, the polynucleotide sequence is read on a substrate on a surface of a structure (also referred to as reaction site herein) or within a feature of a structure (e.g., nanowell, microwell, nanopore, etc.). In some instances, the structure comprises a metal film. In some examples, the structure is a single molecule sequencing chip 203 as illustrated in FIG. 2. In some cases, the polynucleotides are optionally assembled into longer nucleic acids and then sequenced. A polynucleotide ternary complex library 201 is created from the plurality of ternary complexes 111, which is loaded (e.g., immobilized) on a single molecule sequencing chip 203 to be sequenced. In some instances, the polynucleotide ternary complex library 201 comprises at least 100,000, 1 million, 10 million, 50 million, 100 million, 200 million, 500 million, or at least 750 million unique polynucleotides. In some instances, the polynucleotide ternary complex library 201 comprises about 1-750, 1-500, 1-250, 1-100, or 1-10 million unique polynucleotides. In some instances, the polynucleotide ternary complex library 201 comprises no more than 100,000, 1 million, 10 million, 50 million, 100 million, 200 million, 500 million, or at least 750 million unique polynucleotides. The single molecule sequencing chip 203 comprises loci for immobilizing a ternary complex in the ternary complex library 201. In some instances, the single molecule sequencing chip 203 comprises at least 50,000, 100,000, 200,000, 500,000, 750,000, 1 million, 2 million, 5 million, 8 million, 10 million, or at least 20 million loci. In some instances, the single molecule sequencing chip 203 comprises 80,000 to 20 million, 1 million to 20 million, 1 million to 10 million, or 5 million to 20 million loci. In some instances, the single molecule sequencing chip 203 comprises no more than 50,000, 100,000, 200,000, 500,000, 750,000, 1 million, 2 million, 5 million, 8 million, 10 million, or no more than 20 million loci.

Components (e.g., substrates) described herein may be attached or fixed to a surface. In some instances, a substrate (e.g., polynucleotide, polymerase, primer, or a complex of any combination thereof), is immobilized on a surface of a reaction site comprising a material and/or that is coated with a material that facilitates a coupling reaction with the substrate for attachment. In such instances, surface modifications may be employed that chemically and/or physically alter the substrate surface by an additive or subtractive process to change one or more chemical and/or physical properties of a substrate surface or a selected site or region of the surface. For example, surface modification involves (1) changing the wetting properties of a surface, (2) functionalizing a surface, e.g. providing, modifying or substituting surface functional groups, (3) defunctionalizing a surface, e.g. removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. In some instances, the surface of a structure is selectively functionalized to produce two or more distinct areas on a structure, wherein at least one area has a different surface or chemical property that another area of the same structure. Such properties include, without limitation, surface energy, chemical termination, surface concentration of a chemical moiety, and the like. In some instances, a mixture of functional agents may be used to modify the surface. Surfaces of the reaction sites, including for the purpose of substrate immobilization, can be prepared using methods further described herein. In some instances, a surface is re-immobilized with substrate after sequencing.

The immobilization of the polynucleotides on to the sequencing chip can be accomplished through covalent or non-covalent interactions, via a linker moiety or tether, for example, using an enzyme (e.g., polymerase, transcriptase, kinase, etc.) attached to the substrate (e.g., a nucleic acid template, e.g., DNA, RNA, or hybrids, analogs, and mimetics thereof, or a target molecule for a kinase) at a reaction site. In some instances, conjugation chemistry is used to immobilize polynucleotides or other components to the sequencing chip. Conjugation chemistry in some instances comprises nucleophile/carbonyl; an azide/phosphine; 1,4 Michael addition, 1,3-dipolar cycloaddition, inverse electron demand cycloaddition; olefin metathesis; or cross-coupling reaction.

In alternative instances, the substrate, including a polynucleotide or a primer, is directly attached to the reaction site (e.g., not via the enzyme). In some cases, the reaction site is the surface of a single molecule sequencing chip 203 or is within an optical confinement (e.g., microwell, nanowell, nanopore, etc.). Non-limiting examples of binding moieties for attaching nucleic acids or polymerases to a solid support include amide or amino linkages, carbamate linkages, disulfide linkages, ester linkages, functionalized maleimide linkages, hydrazone linkages, (N)-functionalized thiourea, thiolester linkages, streptavidin or avidin/biotin linkages, or a combination thereof. In some instances, antibodies that bind to one or more reaction components are used as the binding moieties. In some instances, a silyl moiety is used to attached to a nucleic acid directly to a substrate of the reaction site, such as glass. In some instances, a nucleic acid template (e.g., polynucleotide) is directly attached to the reaction site. In some instances, a nucleic acid template (e.g., polynucleotide) is immobilized onto a reaction site by attaching a primer comprising a complementary region at the reaction site that is capable of hybridizing with the template, thereby immobilizing it in a position suitable for monitoring. In alternative instances, a nucleic acid template (e.g., polynucleotide) is immobilized onto a reaction site via the polymerase as described herein.

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some instances, conjugation reactions are mediated by chemical reagents such as catalysts, light, or reactive chemical groups found on linkers, conjugation moieties, or unnatural amino acids. In some instances, conjugation reactions are mediated by enzymes. In some instances, a conjugation reaction used herein is described in Gong, Y., Pan, L. Tett. Lett. 2015, 56, 2123. In some instances, a conjugation reaction used herein is described in Chen, X.; Wu. Y-W. Org. Biomol. Chem. 2016, 14, 5417.

In some instances described herein, a conjugation reaction comprises reaction of a ketone or aldehyde with a nucleophile. In some instances, a conjugation reaction comprises reaction of a ketone with an aminoxy group to form an oxime. In some instances, a conjugation reaction comprises reaction of a ketone with an aryl or heteroaryl amine group to form an imine. In some instances, a conjugation reaction comprises reaction of an aldehyde with an aryl or heteroaryl amine group to form an imine. In some instances, a conjugation reaction described herein results in cytokine peptide comprising a linker or conjugation moiety attached via an oxime. In some instances, a conjugation reaction comprises a Pictet-Spengler reaction of an aldehyde or ketone with a tryptamine nucleophile. In some instances, a conjugation reaction comprises a hydrazino-Pictet-Spengler reaction. In some instances, a conjugation reaction comprises a Pictet-Spengler ligation.

In some instances described herein, a conjugation reaction described herein comprises reaction of an azide and a phosphine (Staudinger ligation). In some instances, the phosphine is an aryl phosphine. In some instances, the aryl phosphine comprises an ortho ester group. In some instances, the phosphine comprises the structure methyl 2-(diphenylphosphaneyl)benzoate. In some instances, a conjugation reaction described herein results in cytokine peptide comprising a linker or conjugation moiety attached via an arylamide. In some instances, a conjugation reaction described herein results in cytokine peptide comprising a linker or conjugation moiety attached via an amide.

In some instances described herein, a conjugation reaction described herein comprises a 1,3-dipolar cycloaddition reaction. In some instances, the 1,3-dipolar cycloaddition reaction comprises reaction of an azide and a phosphine ("Click" reaction). In some instances, the conjugation reaction is catalyzed by copper. In some instances, a conjugation reaction described herein results in cytokine peptide comprising a linker or conjugation moiety attached via a triazole. In some instances, a conjugation reaction described herein comprises reaction of an azide with a strained olefin. In some instances, a conjugation reaction described herein comprises reaction of an azide with a strained alkyne. In some instances, a conjugation reaction described herein comprises reaction of an azide with a cycloalkyne, for example, OCT, DIFO, DIFBO, DIBO, BARAC, TMTH, or other strained cycloalkyne, the structures of which are shown in Gong, Y., Pan, L. Tett. Lett. 2015, 56, 2123. In some instances, a 1,3-dipolar cycloaddition reaction is catalyzed by light ("photoclick"). In some instances, a conjugation reaction described herein comprises reaction of a terminal allyl group with a tetrazole and light. In some instances, a conjugation reaction described herein comprises reaction of a terminal alkynyl group with a tetrazole and light. In some instances, a conjugation reaction described herein comprises reaction of an O-allyl amino acid with a tetrazine and light. In some instances, a conjugation reaction described herein comprises reaction of O-allyl tyrosine with a tetrazine and light.

In some instances described herein, a conjugation reaction described herein comprises an inverse-electron demand cycloaddition reaction comprising a diene and a dienophile. In some instances, the diene comprises a tetrazine. In some instances, the dienophile comprises an alkene. In some instances, the dienophile comprises an alkyne. In some instances, the alkyne is a strained alkyne. In some instances, the alkene is a strained diene. In some instances, the alkyne is a trans-cyclooctyne. In some instances, the alkyne is a cyclooctene. In some instances, the alkene is a cyclopropene. In some instances, the alkene is a fluorocyclopropene. In some instances, a conjugation reaction described herein results in the formation of a cytokine peptide attached to a linker or conjugation moiety via a 6-membered ring heterocycle comprising two nitrogen atoms in the ring.

In some instances described herein, a conjugation reaction described herein comprises an olefin metathesis reaction. In some instances, a conjugation reaction described herein comprises reaction of an alkene and an alkyne with a ruthenium catalyst. In some instances, a conjugation reaction described herein comprises reaction of two alkenes with a ruthenium catalyst. In some instances, a conjugation reaction described herein comprises reaction of two alkynes with a ruthenium catalyst. In some instances, a conjugation reaction described herein comprises reaction of an alkene or alkyne with a ruthenium catalyst and an amino acid comprising an allyl group. In some instances, a conjugation reaction described herein comprises reaction of an alkene or alkyne with a ruthenium catalyst and an amino acid comprising an allyl sulfide or selenide. In some instances, a ruthenium catalyst is Hoveda-Grubbs 2nd generation catalyst. In some instances, an olefin metathesis reaction comprises reaction of one or more strained alkenes or alkynes.

In some instances described herein, a conjugation reaction described herein comprises a cross-coupling reaction. In some instances, cross-coupling reactions comprise transition metal catalysts, such as iridium, gold, ruthenium, rhodium, palladium, nickel, platinum, or other transition metal catalyst and one or more ligands. In some instances, transition metal catalysts are water-soluble. In some instances described herein, a conjugation reaction described herein comprises a Suzuki-Miyaura cross-coupling reaction. In some instances described herein, a conjugation reaction described herein comprises reaction of an aryl halide (or triflate, or tosylate), an aryl or alkenyl boronic acid, and a palladium catalyst. In some instances described herein, a conjugation reaction described herein comprises a Sonogashira cross-coupling reaction. In some instances described herein, a conjugation reaction described herein comprises reaction of an aryl halide (or triflate, or tosylate), an alkyne, and a palladium catalyst. In some instances, cross-coupling reactions result in attachment of a linker or conjugating moiety to a cytokine peptide via a carbon-carbon bond.

In some instances described herein, a conjugation reaction described herein comprises a deprotection or "uncaging" reaction of a reactive group prior to conjugation. In some instances, a conjugation reaction described herein comprises uncaging of a reactive group with light, followed by a conjugation reaction. In some instances, a reactive group is protected with an aralkyl moiety comprising one or more nitro groups. In some instances, uncaging of a reactive group results in a free amine, sulfide, or other reactive group. In some instances, a conjugation reaction described herein comprises uncaging of a reactive group with a transition metal catalyst, followed by a conjugation reaction. In some instances, the transition metal catalyst comprises palladium and one or more ligands. In some instances, a reactive group is protected with an allyl moiety. In some instances, a reactive group is protected with an allylic carbamate. In some instances, a reactive group is protected with a propargylic moiety. In some instances, a reactive group is protected with a propargyl carbamate. In some instances, a reactive group is protected with a dienophile, wherein exposure to a diene (such as a tetrazine) results in deprotection of the reactive group.

In some instances described herein, a conjugation reaction described herein comprises a ligand-directed reaction, wherein a ligand (optionally) attached to a reactive group) facilitates the site of conjugation between the reactive group and the cytokine peptide. In some instances, the ligand is cleaved during or after reaction of the cytokine peptide with the reactive group. In some instances, the conjugation site of the cytokine peptide is a natural amino acid. In some instances, the conjugation site of the cytokine peptide is a lysine, cysteine, or serine. In some instances, the conjugation site of the cytokine peptide is an unnatural amino acid described herein. In some instances the reactive group comprises a leaving group, such as an electron-poor aryl or heteroaryl group. In some instances the reactive group comprises a leaving group, such as an electron-poor alkyl group that is displaced by the cytokine peptide. In some instances, a conjugation reaction described herein comprises reaction of a radical trapping agent with a radical species. In some instances, a conjugation reaction described herein comprises an oxidative radical addition reaction. In some instances, a radical trapping agent is an arylamine. In some instances, a radical species is a tyrosyl radical. In some instances, radical species are generated by a ruthenium catalyst (such as [Ru(bpy)3]) and light.

Enzymatic reactions are optionally used for conjugation reactions described herein. Exemplary enzymatic conjugations include SortA-mediated conjugation, a TGs-mediated conjugation, or an FGE-mediated conjugation. In some instances, a conjugation reaction described herein comprises native protein ligation (NPL) of a terminal 1-amino-2-thio group with a thioester to form an amide bond.

Various conjugation reactions are described herein for reacting a linker or conjugating moiety with a cytokine peptide, wherein the reaction occurs with a natural ("canonical") amino acid in the cytokine peptide. In some instances, the natural amino acid is found at a conjugation position is found in a wild type sequence, or alternatively the position has been mutated. In some instances, a conjugation reaction comprises formation of a disulfide bond at a cysteine residue. In some instances, a conjugation reaction comprises a 1,4 Michael addition reaction of a cysteine or lysine. In some instances, a conjugation reaction comprises a cyanobenzothiazole ligation of a cysteine. In some instances, a conjugation reaction comprises crosslinking with an acetone moiety, such as 1,3-dichloro-2-propionone. In some instances, a conjugation reaction comprises a 1,4 Michael addition to a dehydroalanine, formed by reaction of cysteine with O-mesitylenesulfonylhydroxylamine. In some instances a conjugation reaction comprises reaction of a tyrosine with a triazolinedione (TAD), or TAD derivative. In some instances a conjugation reaction comprises reaction of a tryptophan with a rhodium carbenoid.

In some cases, the polymerase comprises the first moiety, which is used to tether the ternary complex directly to the single molecule sequencing chip 203. In some instances, a binding molecule is attached to the first moiety, which is used to tether the ternary complex to the single molecule sequencing chip 203. In further cases, the single molecule sequencing chip 203 comprises a plurality of second moieties on its reaction sites. In some examples, the second moiety is biotin. In some examples, the second moiety is a protein. In some examples, the second moiety is an oligonucleotide. In some cases, the plurality of second moieties is used to tether the ternary complex to the single molecule sequencing chip 203, either via the polynucleotide, polymerase, primer, or a combination thereof. In further cases, the plurality of second moieties are attached to the binding molecule attached to the first moieties, or are attach directly to the first moieties (e.g., without the binding molecule). In some examples, the first and the second moieties are the same moiety. In alternative examples, the first and the second moieties are different moieties. In some instances, the single molecule sequencing chip 203 is "loaded" or populated to a capacity with sample polynucleotides. In some instances, one or more loci each comprise a single molecule sample polynucleotide. In some instances, the single molecule sequencing chip 203 is loaded at about 1%, 2%, 5%, 10%, 20%, 30%, 40%, 50%, 60%, or 70% capacity. In some instances, the single molecule sequencing chip 203 is loaded at about 33%, about 50%, or about 66% capacity. In some instances, the single molecule sequencing chip 203 is loaded at no more than 1%, 2%, 5%, 10%, 20%, 30%, 40%, 50%, 60%, or 70% capacity. In some instances, the single molecule sequencing chip 203 is loaded at about 1-50%, 2-50%, 5-50%, 5-25%, 5-10%, 10 to 50% capacity, about 10 to 40% capacity, about 10 to 30% capacity, about 20 to 40% capacity, about 20 to 30% capacity, about 30 to 40% capacity, or about 30 to 50% capacity. In some examples, the single molecule sequencing chip 203 is loaded as an array according to a predetermined distribution. In some examples, the single molecule sequencing chip 203 is loaded according to a Poisson distribution or a normal distribution.

The polynucleotides now on the loaded single molecule sequencing chip 203 are then sequenced 204, resulting an output signal 205 unique to the nucleotides incorporated during sequencing. The output signals are used to determine the sequence of the polynucleotide via sequence complementarity. In some instances, the polynucleotides being sequenced comprise no more than 30,000, 20,000, 10,000, 5,000, 1000, 500, or no more than 250 bases. In some instances, the polynucleotides being sequenced comprise at least 30,000, 20,000, 10,000, 5,000, 1000, 500, or at least 250 bases. Once the polynucleotides on the sequencing chip have been sequenced, the ternary complexes are removed 206 through a washing step 207. In some instances, the surface of the unloaded single molecule sequencing chip 208 does not have to be re-functionalized following the washing step 207. In some cases, the plurality of second moieties remain tethered to an unloaded (or at least partially unloaded) single molecule sequencing chip 208 following the washing step 207. In some instances, the washing step 207 comprises one or more of organic solvent(s), heat, or enzymes. In some instances, the organic solvent(s) comprises MeCN, methanol, ethanol, 2-propanol, acetone, DMF, DMSO, formamide, THF, or any combination thereof. In some cases, the enzyme is a proteinase. In some cases, the proteinase comprises an aminopeptidase. In some cases, the aminopeptidase comprises proteinase K, N-terminal aminopeptidases, C-terminal aminopeptidases, chymotrypsin, trypsin, pepsin, or LysC. In some examples, the proteinase is proteinase K. In some instances, the washing step 207 comprises use of liquid comprising biotin to disrupt streptavidin or avidin/biotin linkages. In some instances, the washing step 207 takes no more than 1 minute, 2 minutes, 3 minutes, 4 minutes, 5 minutes, 6 minutes, 7 minutes, 8 minutes, 9 minutes, or 10 minutes. In some instances, the washing step 207 takes about 1 to 10 minutes, about 1 to 7 minutes, about 1 to 5 minutes, about 1 to 2 minutes, about 2 to 6 minutes, about 3 to 4 minutes, about 5 to 6 minutes, 5 to 10 minutes, or 7 to 10 minutes. In some instances, the full cycle of sequencing the polynucleotide ternary complex library 201 and washing the single molecule sequencing chip 203 takes no more than 5 minutes, 6 minutes, 7 minutes, 8 minutes, 9 minutes, 10 minutes, 11 minutes, 12 minutes, 13 minutes, 14 minutes, 15 minutes, 18 minutes, 20 minutes, 25 minutes, or 30 minutes. The washing may comprise repeated contact with washing conditions, such that washing is repeated 1, 2, 3, 4, 5, 8, 10, 12, 15, 20, 25, 30, 50, or 100 times. The washing may comprise repeated contact with washing conditions, such that washing is repeated at least 1, 2, 3, 4, 5, 8, 10, 12, 15, 20, 25, 30, 50, or at least 100 times. In some instances, the removed ternary complexes are recovered. In alternative instances, the removed ternary complexes are not recovered. Referring to FIG. 2, once all the ternary complexes have been removed in the washing step 207, the unloaded single molecule sequencing chip 208 is reloaded 209 with a new ternary complex library. In some instances, the surface of the unloaded single molecule sequencing chip 208 is conditioned before being reloaded. In some instances, the surface of the unloaded single molecule sequencing chip 208 is not conditioned before being reloaded. In some instances, conditioning comprises bathing, baking, cleaning, etching, washing, or otherwise resorting the surface to a condition suitable for subsequent polynucleotide sequencing. Once a new ternary complex library 209 is reloaded for sequencing, and the sequencing steps as described herein are repeated. The number of times a surface is reused and the methods for recycling/preparing the surface for reuse vary depending on subsequent applications. Surfaces prepared for reuse are, in some instances, reused at least 1, 2, 3, 5, 10, 20, 50, 100, 1,000 or more times. In some instances, the remaining "life" or number of times a surface is suitable for reuse is measured or predicted. In some instances the sequencing method comprises one or more steps of (a) contacting a plurality of polynucleotides with at least one primer and at least one polymerase to form a plurality of ternary complexes; (b) detecting one or more bases of the polynucleotides, wherein detection occurs when the plurality of ternary complexes are bound to a surface; (c) removing the ternary complexes from the surface; and (d) repeating steps a-c to sequence the polynucleotides, wherein the method comprises at least one washing step.

Any number of reads may be acquired before the surface of a device is reloaded with new components (e.g., primers, polymerases, sample polynucleotides). In some instances, at least 10 million, 50 million, 100 million, 1 billion, 10 billion, 100 billion, or at least 200 billion reads are acquired before the device is reloaded. In some instances, a read comprises a segment of nucleic sequence data. In some instances a read is at least 10, 50, 75, 100, 125, 150, 200, 250, 500, 1000, 2000, 5000, or at least 10,000 bases in length. In some instances, reads are assembled in silico into larger contiguous sequences (e.g., contigs). In some instances, contigs are assembled in silico into larger groups such as chromosomes, genomes, data files, or other units. In some instances, the reads are assembled using one or more indices. In some instances, the one or more indices indicates a location or address of the digital information encoded in a nucleic acid sequence.

Sequencing methods described herein may comprise use of luminescent markers to sequence polynucleotides. In some cases, each nucleotide, A, T, C, and G, in a reaction mixture is labeled with a unique luminescent marker. Examples of luminescent markers comprise, but are not limited to enzymes, fluorescent molecules, fluorophores, fluorescent dyes, fluorescent stains, dyes (e.g., organic dyes or non-organic dyes), fluorescent proteins (e.g., intrinsic or non-intrinsic), non-fluorescent tags (e.g., surface enhanced Raman scattering (SERS) particles), scattering metallic nanoparticles (e.g., gold or silver), combinations of chromophores (e.g., fluorescence resonance energy transfer (FRET) labels on a single or multiple components), quantum dots, or a combination thereof. In some instances, each of the unique luminescent markers vary in their emission characteristics, such as emission wavelength, temporal characteristics of emission (e.g., emission decay time periods), and/or response to excitation energy (e.g., probability of absorbing an excitation photon). In some cases, the differences in any one of each luminescent marker's emission characteristics allow them to be discriminated from one another. In some examples, measurements of time variations in the emitted luminescence (e.g., fluorescence lifetimes) is used to discriminate between luminescent markers. In some instances, the luminescent marker is attached to the nucleotide through a linker, for example to the terminal phosphate of the nucleotide. Examples of a linker are, but are not limited to, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. The polynucleotide, primer, or polymerase are, in some cases, tethered to a well on the sequencing chip forming a zero-mode waveguide. In some examples, the well (e.g., nanowell) is a cylindrical shape with a diameter. In some examples, the zero-mode waveguide forms in a single metal layer that does not support a propagating optical mode through the well. In some instances, each well on a chip contains about one sample (e.g., one polynucleotide). New nucleotides with unique luminescence markers are consecutively incorporated into the sequence of polynucleotides via a polymerase and a primer. The unique luminescent marker associated with each incorporated nucleotide is excited with at least one appropriate excitation source (e.g., light source, such as a laser) during or after its incorporation. In some instances, the excitation source produces electromagnetic energy that induces an excitation. In some instances, excitation energy from the at least one excitation source is pulsed. In some instances, the at least one excitation source produces more than one excitation energies. The emission from the luminescent marker is subsequently detected and is attributed to a particular nucleotide incorporated. The sequence obtained from the collection of detected luminescent markers is used to determine the sequence of the polynucleotide via sequence complementarity. Following the detection of the luminescent marker, the linker is cleaved in order to separate a luminescent marker from the newly incorporated nucleotide. In some instances, the luminescent marker is attached to the terminal phosphate and a polymerization enzyme, such as polymerase, is used to cleave the luminescent marker.

Further sequencing methods described herein may comprise use of electronics to sequence polynucleotides. In such instances, a molecular electronics sensor is used to produce distinguishable signals depending on the patterns of nucleotides in a polynucleotide sequence. The molecular electronic sensor comprises a pair of electrodes that are spaced apart. A molecular complex is attached to each electrode, forming a molecular electronics circuit. In some instances, the molecular complex comprises a bridge molecule and a probe molecule. Non-limiting examples of the bridge molecule are a graphene nanoribbon, an antibody, a carbon nanotube, a Fab arm of an antibody, a double stranded DNA oligomer, a protein alpha helix, or a combination thereof. In some instances, the probe molecule is a polymerase, which modulates the measurable electrical parameter through its activity. In some cases, the measurable electrical parameter comprises a current between the electrodes that runs through the molecular complex, which either is used to quantitatively (e.g., peak amplitude, signal duration, and the like) and/or qualitatively (e.g., peak shape) distinguish nucleotide patterns. The distinguishable measured electrical parameters are converted into binary data, which are related to the polynucleotide sequence.

Further sequencing methods described herein may comprise a use of nanopore sequencing by synthesis (SBS). In such instances, an enzyme (e.g., polymerase) is used to synthesize a polynucleotide sequence complementary to a target sequence template. Concurrently, identities of each of the nucleotides added to the growing strand are determined by monitoring current flow (e.g., AC or DC) through a nanopore adjacent to the polymerase active site. A tag is attached to each added nucleotide, which is used to produce identifiable changes in the current flowing through the nanopore. Examples of tags include, but are not limited to, a polyethylene-glycol (PEG) oligomer, an organic dye moiety, an oligonucleotide (including natural and/or non-natural analog monomer units), a polypeptide (including natural and/or non-natural analog monomer units), an oligomeric moiety, or any combination thereof. In some instances, a tag resides in the nanopore for a sufficient amount of time (e.g., "dwell time") as to provide an identifiable blockage of current through the nanopore (e.g., "blocking current"). The blocking current is used to identify the specific nucleotide associated with the tag as to distinguish it from the other tagged nucleotides.

Additional computer-integrated methods may be used with the sequencing methods described herein. In some instances, an algorithm comprising machine learning (ML) is used to associate the electrical currents/voltages to the nucleoside monomer added to the polynucleotide. In some cases, the algorithm comprising ML may be trained with training data in order to associate the electrical currents/voltages to the nucleoside monomer added to the polynucleotide. In some cases, the algorithm comprises classical ML algorithms for classification and/or clustering (e.g., K-means clustering, mean-shift clustering, density-based spatial clustering of applications with noise (DBSCAN), expectation-maximization (EM) clustering, agglomerative hierarchical clustering, logistic regression, naïve Bayes, K-nearest neighbors, random forests or decision trees, gradient boosting, support vector machines (SVMs), or a combination thereof).

In some cases, the algorithm comprises a learning algorithm comprising layers, such as one or more neural networks. Neural networks may comprise connected nodes in a network, which may perform functions, such as transforming or translating input data. In some examples, the output from a given node may be passed on as input to another node. In some embodiments, the nodes in the network may comprise input units, hidden units, output units, or a combination thereof. In some cases, an input node may be connected to one or more hidden units. In some cases, one or more hidden units may be connected to an output unit. The nodes may take in input and may generate an output based on an activation function. In some embodiments, the input or output may be a tensor, a matrix, a vector, an array, or a scalar. In some embodiments, the activation function may be a Rectified Linear Unit (ReLU) activation function, a sigmoid activation function, or a hyperbolic tangent activation function. In some embodiments, the activation function may be a Softmax activation function. The connections between nodes may further comprise weights for adjusting input data to a given node (e.g., to activate input data or deactivate input data). In some embodiments, the weights may be learned by the neural network. In some embodiments, the neural network may be trained using gradient-based optimizations. In some cases, the gradient-based optimization may comprise of one or more loss functions. In some examples, the gradient-based optimization may be conjugate gradient descent, stochastic gradient descent, or a variation thereof (e.g., adaptive moment estimation (Adam)). In further examples, the gradient in the gradient-based optimization may be computed using backpropagation. In some embodiments, the nodes may be organized into graphs to generate a network (e.g., graph neural networks). In some embodiments, the nodes may be organized into one or more layers to generate a network (e.g., feed forward neural networks, convolutional neural networks (CNNs), recurrent neural networks (RNNs), etc.). In some cases, the neural network may be a deep neural network comprising of more than one layer.

In some cases, the neural network may comprise one or more recurrent layer. In some examples, the one or more recurrent layer may be one or more long short-term memory (LSTM) layers or gated recurrent unit (GRU), which may perform sequential data classification and clustering. In some embodiments, the neural network may comprise one or more convolutional layers. The input and output may be a tensor representing of variables or attributes in a data set (e.g., features), which may be referred to as a feature map (or activation map). In some cases, the convolutions may be one dimensional (1D) convolutions, two dimensional (2D) convolutions, three dimensional (3D) convolutions, or any combination thereof. In further cases, the convolutions may be 1D transpose convolutions, 2D transpose convolutions, 3D transpose convolutions, or any combination thereof. In some examples, one-dimensional convolutional layers may be suited for time series data since it may classify time series through parallel convolutions. In some examples, convolutional layers may be used for analyzing electrical currents/voltages to the nucleoside monomer added to the polynucleotide.

The layers in a neural network may further comprise one or more pooling layers before or after a convolutional layer. The one or more pooling layers may reduce the dimensionality of the feature map using filters that summarize regions of a matrix. This may down sample the number of outputs, and thus reduce the parameters and computational resources needed for the neural network. In some embodiments, the one or more pooling layers may be max pooling, min pooling, average pooling, global pooling, norm pooling, or a combination thereof. Max pooling may reduce the dimensionality of the data by taking only the maximums values in the region of the matrix, which helps capture the significant feature. In some embodiments, the one or more pooling layers may be one dimensional (1D), two dimensional (2D), three dimensional (3D), or any combination thereof. The neural network may further comprise of one or more flattening layers, which may flatten the input to be passed on to the next layer. In some cases, the input may be flattened by reducing it to a one-dimensional array. The flattened inputs may be used to output a classification of an object (e.g., classification of electrical currents/voltages to a nucleoside monomer added to the polynucleotide, etc.). The neural networks may further comprise one or more dropout layers. Dropout layers may be used during training of the neural network (e.g., to perform binary or multi-class classifications). The one or more dropout layers may randomly set certain weights as 0, which may set corresponding elements in the feature map as 0, so the neural network may avoid overfitting. The neural network may further comprise one or more dense layers, which comprise a fully connected network. In the dense layer, information may be passed through the fully connected network to generate a predicted classification of an object, and the error may be calculated. In some embodiments, the error may be backpropagated to improve the prediction. The one or more dense layers may comprise a Softmax activation function, which may convert a vector of numbers to a vector of probabilities. These probabilities may be subsequently used in classifications, such as classifications of electrical currents and/or voltages to the nucleoside monomer added to the polynucleotide.

Nucleic Acid Based Information Storage

Provided herein are devices, compositions, systems and methods for nucleic acid-based information (data) storage. In a first step, a digital sequence encoding an item of information (e.g., digital information in a binary code for processing by a computer) is received. An encryption scheme is applied to convert the digital sequence from one or more symbols (e.g., a binary code) to a nucleic acid sequence. In one example, a surface material for nucleic acid extension, a design for loci for nucleic acid extension (aka, arrangement spots), and reagents for nucleic acid synthesis are selected. The surface of a structure is prepared for nucleic acid synthesis. De novo polynucleotide synthesis is then performed. In another example, the digital sequence is represented by a set of pre-synthesized nucleic acids. In some instances, the pre-synthesized nucleic acids are attached to each other to form larger nucleic acids representing the item of information. In some instances, attachment is performed with ligases or amplification (e.g., PCR). The synthesized polynucleotides are stored and available for subsequent release, in whole or in part. Once released, the polynucleotides, in whole or in part, are sequenced using the methods described herein, and subject to decryption to convert nucleic sequence back to digital sequence. The digital sequence is then assembled to obtain an alignment encoding for the original item of information. In some instances, digital information does not comprise genetic information obtained from a naturally occurring genome of an organism.

Nucleic acids encoding digital information may comprise error correction component. In some instances, the error correction component comprises an error correction code, such as a Reed-Solomon (RS) code, a LDPC code, a polar code, a turbo code. In some instances, the error correction code spreads the digital data to be stored over many polynucleotides. In some instances, spreading the data over a plurality of polynucleotides builds redundancy to correct for erasures (e.g., lost oligos). In some instances, the digital information can be recovered in the presence of errors. In some instances, the error correction component comprises a parity base. In some instances, the error correction component comprises an index sequence. In some instances, the index sequences define the location or address of the digital information encoded in the nucleic acid. In some instances, the index sequences define the source of the digital information. Nucleic acids encoding digital information in some instances comprise overlap with one or more nucleic acids in the same library or set. In some instances, the error correction component comprises an overlap or redundancy region. In some instances, algorithms are applied to sequenced nucleic acids to reduce errors. In some instances, error corrective algorithms comprise consensus sequencing, HEDGES (Hash Encoded, Decoded by Greedy Exhaustive Search), or other method.

Nucleic acids encoding for digital information may be stored in different media. In some instances, nucleic acids are stored as essentially dry or lyophilized powders. In some instances, nucleic acids are stored in buffers. In some instances, nucleic acids are stored on chips, wafers, or other silicon solid support. In some instances, nucleic acids are stored inside an organism (or population of organisms), such as a plasmid or genome.

Items of Information

Optionally, an early step of data storage process disclosed herein includes obtaining or receiving one or more items of information in the form of an initial code. Items of information include, without limitation, text, audio and visual information. Exemplary sources for items of information include, without limitation, books, periodicals, electronic databases, medical records, letters, forms, voice recordings, animal recordings, biological profiles, broadcasts, films, short videos, emails, bookkeeping phone logs, internet activity logs, drawings, paintings, prints, photographs, pixelated graphics, and software code. Exemplary biological profile sources for items of information include, without limitation, gene libraries, genomes, gene expression data, and protein activity data. Exemplary formats for items of information include, without limitation, .txt, .PDF, .doc, .docx, .ppt, .pptx, .xls, .xlsx, .rtf, .jpg, .gif, .psd, .bmp, .tiff, .png, and. mpeg. Digital information in some instances is obtained from magnetic media, flash memory, cloud storage, or stored nucleic acids. The amount of individual file sizes encoding for an item of information, or a plurality of files encoding for items of information, in digital format include, without limitation, up to 1024 bytes (equal to 1 KB), 1024 KB (equal to 1 MB), 1024 MB (equal to 1 GB), 1024 GB (equal to 1 TB), 1024 TB (equal to 1 PB), 1 exabyte, 1 zettabyte, 1 yottabyte, 1 xenottabyte or more. In some instances, an amount of digital information is at least 1 gigabyte (GB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 gigabytes. In some instances, the amount of digital information is at least 1 terabyte (TB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 terabytes. In some instances, the amount of digital information is at least 1 petabyte (PB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 petabytes. In some instances, the amount of digital information is at least 1, 2, 3, 4, 5, 6, 7, 8, 9, 10, 20, 50, 100, 200, 300, 400, 500, 600, 700, 800, 900, 1000 or more than 1000 zettabytes. In some instances, the digital information does not contain genomic data acquired from an organism. In some instances, a two bit per base, three bit per base (e.g., Huffman), comma coding (reading frames of six codons with isothermal melting temperatures, alternating code, comma-free code, perfect genetic code (variable codon length) or other encoding method is used. In some instances, digital information is further encrypted with a key or obscured using steganography.

Devices and methods described herein may increase sequencing or “reading” rates for digital information stored in nucleic acids. In some instances 1 Mb of data is acquired in no more than 15 minutes, 20 minutes, 25 minutes, 30 minutes, 35 minutes, 40 minutes, or 1 hour. In some instances, at least 1, 2, 3, 4, 5, 7, 10, 12, 15, 20, 25, or at least 30 terabytes of data are read within 24 hours. In some instances 1 Gb of data is acquired in no more than 15 minutes, 20 minutes, 25 minutes, 30 minutes, 35 minutes, 40 minutes, or 1 hour. In some instances, at least 1, 2, 3, 4, 5, 7, 10, 12, 15, 20, 25, or at least 30 terabytes of data are read within 24 hours. In some instances, 1-50, 1-30, 1-20, 1-15, 1-10, 1-5, 5-20, 5-30, 10-50, 10-25, 20-30, or 20-50 terabytes of data are read within 24 hours. In some instances, at least 1, 2, 3, 4, 5, 7, 10, 12, 15, 20, 25, or at least 30 terabytes of data are read within 24 hours on a device having pitch distance (distance between independently readable loci) of no more than 100, 75, 50, 25, 20, 15, 10, 5, 2 or 1 microns. In some instances, at least 1, 2, 3, 4, 5, 7, 10, 12, 15, 20, 25, or at least 30 terabytes of data are read within 24 hours on a device having pitch distance of no more than 1000, 900, 800, 700, 600, 500, 400, 300, 200, 100, 75, 50, 25, 20, 15, or 10 nm. In some instances, at least 1, 2, 3, 4, 5, 7, 10, 12, 15, 20, 25, or at least 30 petabytes of data are read within 24 hours on a device having pitch distance (distance between independently readable loci) of no more than 100, 75, 50, 25, 20, 15, 10, 5, 2 or 1 microns. In some instances, at least 1, 2, 3, 4, 5, 7, 10, 12, 15, 20, 25, or at least 30 zettabytes of data are read within 24 hours on a device having pitch distance (distance between independently readable loci) of no more than 100, 75, 50, 25, 20, 15, 10, 5, 2 or 1 microns.

Devices and methods described herein may increase sequencing or “reading” fidelity for digital information stored in nucleic acids. In some instances, digital information is recovered with an error rate (per base) of no more than 10%, 5%, 4%, 3% 2%, 1.5%, 1%, 0.5%, 0.2%, 0.1%, 0.01%, 0.001%, or no more 0.0001%. In some instances, digital information is recovered with an error rate (per base) of 0.0001-0.001%, 0.0001-0.01%, 0.001-1%, 0.001-2%, 0.1-2%, 0.1-1%, 0.1-5%, 0.1-2%, or 0.01-2%. In some instances, digital information is recovered with an error rate (per base) of no more than 10%, 5%, 4%, 3% 2%, 1.5%, 1%, 0.5%, 0.2%, 0.1%, 0.01%, 0.001%, or no more 0.0001% prior to processing with an error-correcting algorithm.

Polynucleotides may be designed to collectively span a large region of a predetermined sequence that encodes for digital information. In some instances, larger polynucleotides are generated through ligation reactions to join the synthesized polynucleotides. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adapter sequences is amplified in a polymerase chain reaction (PCR) which includes modified primers that hybridize to the adapter sequences. In some cases, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA. Error correction may be performed on polynucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Thermus aquaticus*) is used to remove failure products from a population of synthesized products. In some instances, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

Digital information may be stored in a plurality of polynucleotides. In some instances, the plurality of polynucleotides comprises about 10,000, 20,000, 50,000, 70,000, 100,000, 120,000, 150,000, or 200,000 unique polynucleotides. In some instances, the plurality of polynucleotides comprises at least about 10,000, 20,000, 50,000, 70,000, 100,000, 120,000, 150,000, or 200,000 unique polynucleotides. In some instances, the plurality of polynucleotides are about 10, 50, 100, 200, 300, 500, 700, 1,000, 5,000, 10,000, 15,000, 20,000, 25,000, 30,000, 35,000, 40,000, or 50,000 bases in length. In some instances, the plurality of polynucleotides are at least about 10, 50, 100, 200, 300, 500, 700, 1,000, 5,000, 10,000, 15,000, 20,000, 25,000, 30,000, 35,000, 40,000, or 50,000 bases in length. In some instances, the plurality of polynucleotides are at most about 10, 50, 100, 200, 300, 500, 700, 1,000, 5,000, 10,000, 15,000, 20,000, 25,000, 30,000, 35,000, 40,000, or 50,000 bases in length.

Structures for Polynucleotide Sequencing

Provided herein are rigid or flexibles structures for polynucleotide sequencing. In the case of rigid structures, provided herein are devices having a structure for the generation of a library of polynucleotides. In some instances, the structure comprises a plate. In some cases, the structure comprises a plate with wells (e.g., nanowells). In some instances, the structure comprises a solid support with a surface comprising a plurality of loci. In some cases, the plurality of loci are arranged in an array laid out on the structure. In some cases, the solid support comprises glass and/or silicon. In some cases, an attachment moiety is covering at least some of the loci. In some examples, the attachment moiety is configured to bind to one or more polynucleotides, polymerases, primers, and a complex of any combination thereof using methods as described herein. In some instances, the surface is reusable. In some cases, the surface is washed, treated, and/or conditioned prior to reuse. In some cases, surface is reusable without removal of the attachment moiety and/or chemical modification. In some instances, the structure comprises a detector that is configured to discriminate the identity of one or more bases added by the polymerase using methods as described herein. In some cases, the detector comprises a plurality of optical detectors. In some cases, the detector comprises a plurality of zero-mode waveguides. In some cases, the detector comprises an optical detector, an electrical detector, or a combination thereof. In some examples, the optical detector is configured to measure various intensities and/or wavelengths. In some examples, the optical detector is configured to measure visible light and/or UV light. In some examples, the optical detector is configured to measure fluorescence. In some examples, the electrical detector is configured to measure changes in voltage or current. In some instances, the structure comprises a flow cell. In some cases, a liquid is continuously flowed in the flow cell. In some examples, the liquid flowing in the flow cell comprises nucleotides or molecules comprising nucleotides (e.g., polynucleotides or nucleic acid, e.g., DNA, RNA, hybrids, analogs, and mimetics thereof). In some instances, the structure may be used for polynucleotide synthesis in addition to polynucleotide sequencing.

Figure 3A:
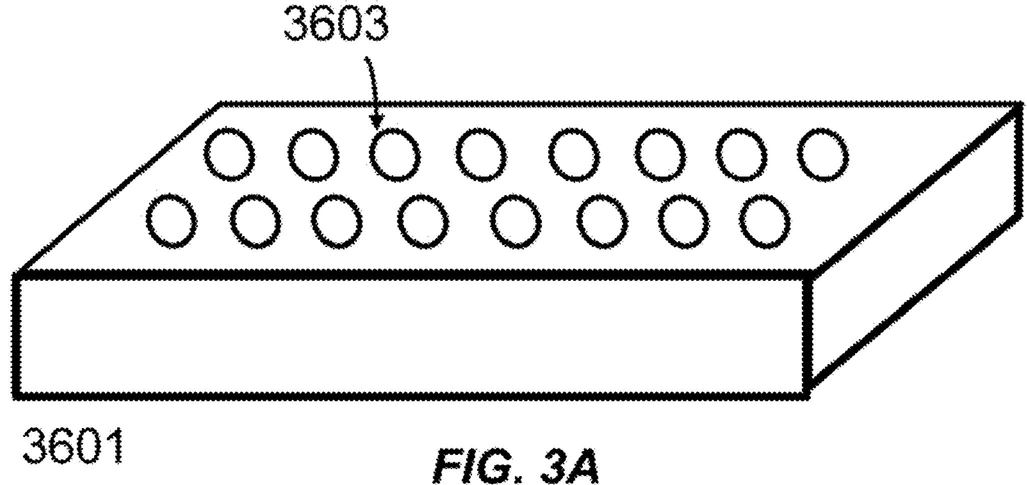
FIGS. 3A-3C depict a zoom in of a flexible structure, having spots, channels, or wells, respectively.
Figure 3B:
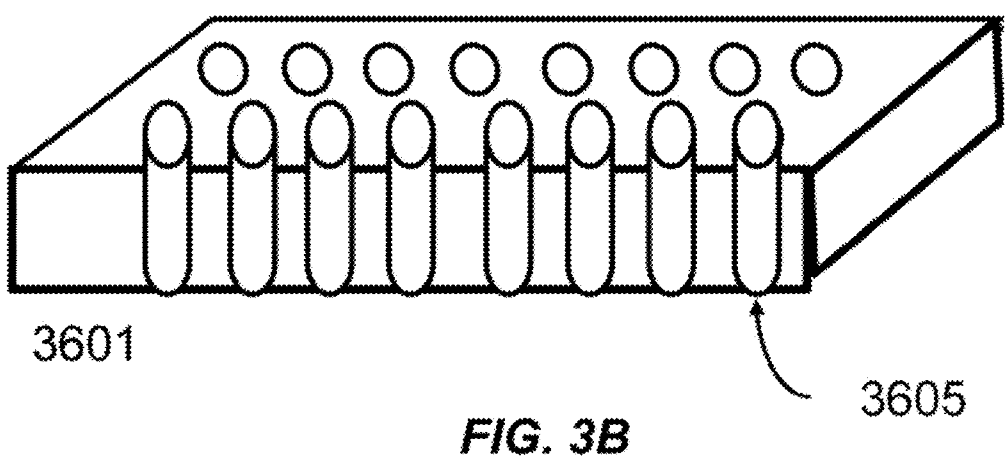
Figure 3C:
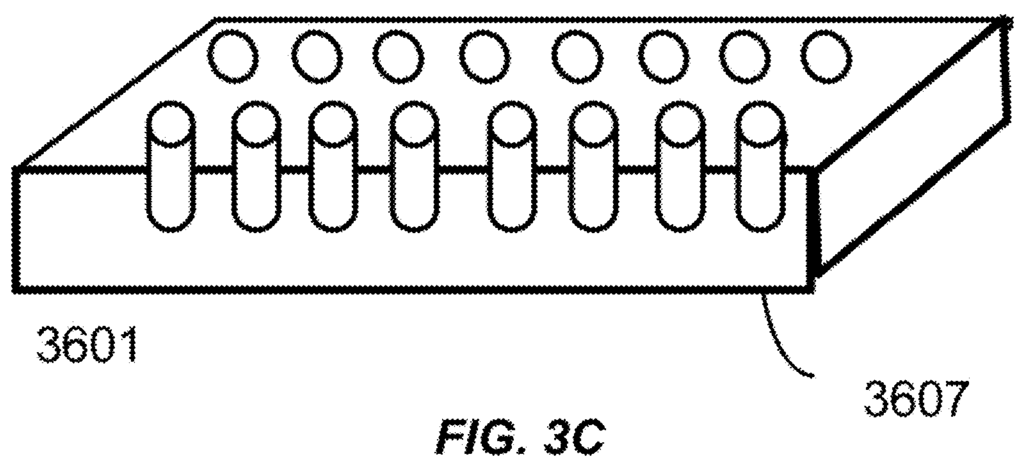
Figure 4A:
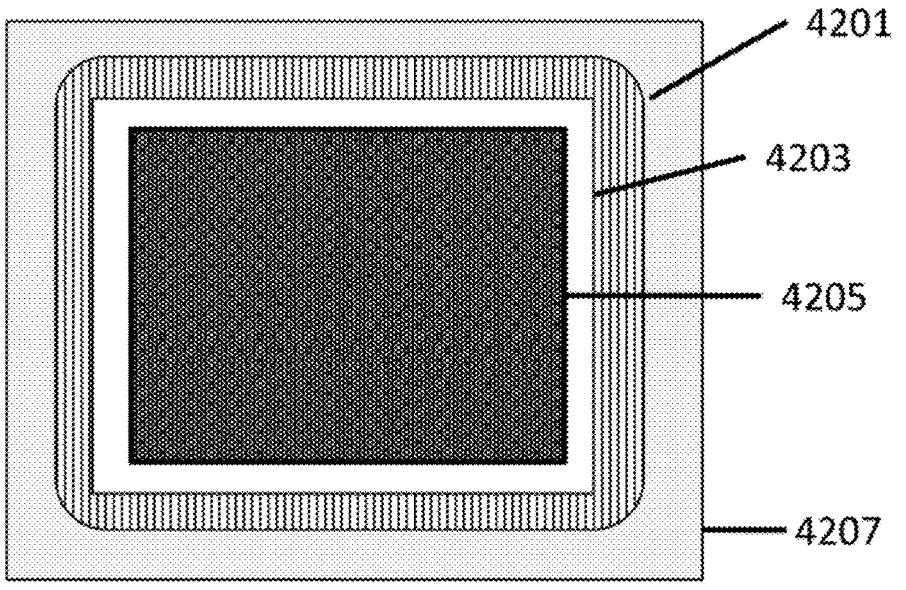
FIG. 4A is a schema of solid support comprising an active area and fluidics interface.
Figure 4B:
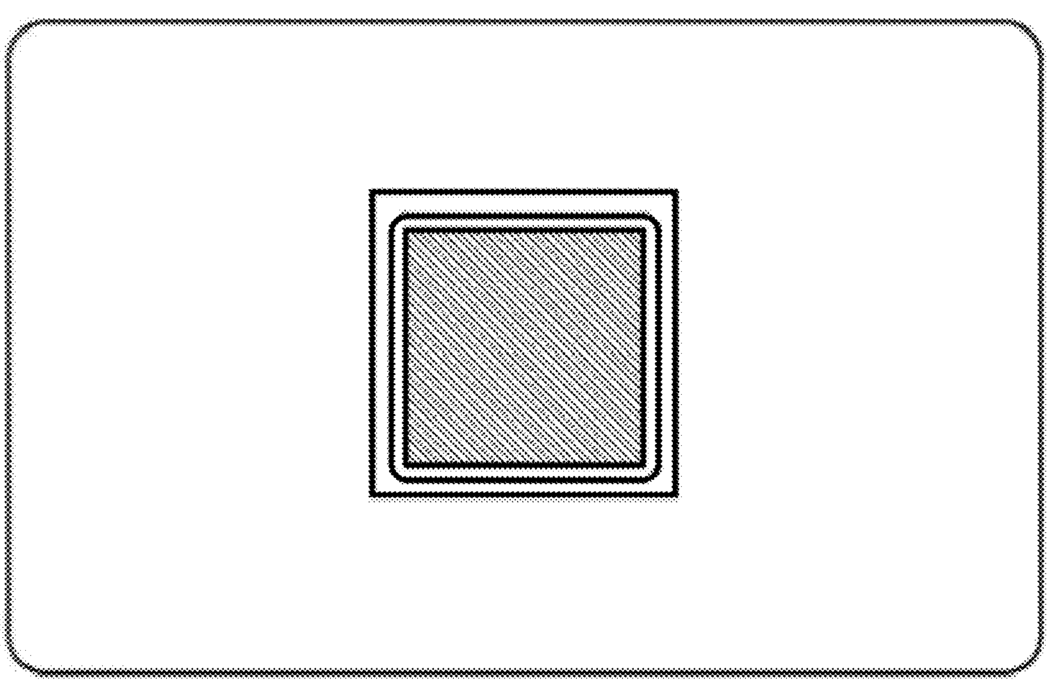
FIG. 4B is a front side of an example of a solid support array. Such arrays in some instances may comprise thousands or millions of polynucleotide synthesis devices as described herein.
Figure 4C:
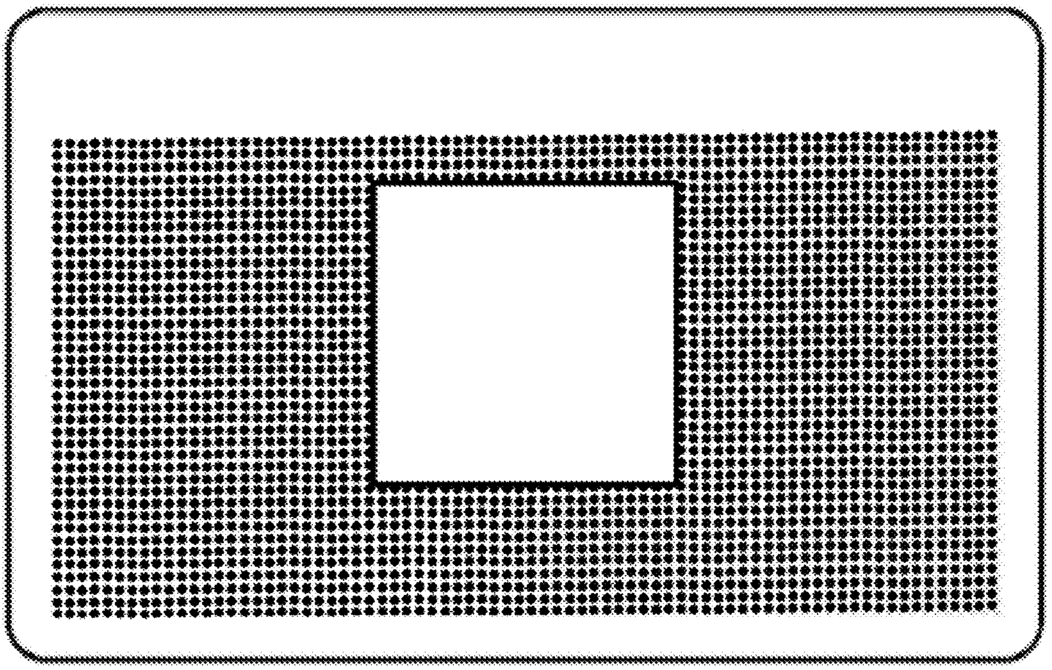
FIG. 4C is a back side of an example of a solid support array.

FIGS. 3A-3C show a zoom in of the loci located on structure for polynucleotide sequencing. Each locus in a portion of the structure 3601, may be a substantially planar spot 3603 (e.g., flat), a channel 3605, or a well 3607. In some instances, the loci are arranged in an array such that each locus of the structure has a width of about 10 um and a distance between the center of each structure of about 21 um. In some instances, each locus of the structure has a width of about 1 um and a distance between the center of each structure of about 2 um. In some instances, each locus of the structure has a width of about 0.1 um and a distance between the center of each structure of about 0.2 um. Loci may comprise, without limitation, circular, rectangular, tapered, or rounded shapes. In some instances, the structure is flexible. Alternatively or in combination, the structures are rigid. In some instances, the rigid structures comprise loci for polynucleotide sequencing. In some instances, the rigid structures comprise substantially planar regions, channels, or wells for polynucleotide sequencing.

Wells described herein may comprise any sizes or dimensions. In some instances, a well described herein has a width to depth (or height) ratio of 1 to 0.01, wherein the width is a measurement of the width at the narrowest segment of the well. In some instances, a well described herein has a width to depth (or height) ratio of 0.5 to 0.01, wherein the width is a measurement of the width at the narrowest segment of the well. In some instances, a well described herein has a width to depth (or height) ratio of about 0.01, 0.05, 0.1, 0.15, 0.16, 0.2, 0.5, or 1. Provided herein are structures for polynucleotide sequencing comprising a plurality of discrete loci for polynucleotide sequencing. Exemplary structures for the loci include, without limitation, substantially planar regions, channels, wells or protrusions. Structures described herein are may comprise a plurality of clusters, each cluster comprising a plurality of wells, loci or channels. Alternatively, described herein are may comprise a homogenous arrangement of wells, loci or channels. Structures provided herein may comprise wells having a height or depth from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some instances, the height of a well is less than 100 um, less than 80 um, less than 60 um, less than 40 um or less than 20 um. In some instances, well height is about 10, 20, 30, 40, 50, 60, 70, 80, 90, 100, 200, 300, 400, 500 um or more. In some instances, the height or depth of the well is at least 10, 25, 50, 75, 100, 200, 300, 400, 500, 600, 700, 800, 900, 1000, or more than 1000 nm. In some instances, the height or depth of the well is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the height or depth of the well is in a range of about 50 nm to about 1 um. In some instances, well height is about 10, 20, 30, 40, 50, 60, 70, 80, 90, 100, 200, 300, 400, 500, 700, 800, 900 or about 1000 nm.

Structures for polynucleotide sequencing provided herein may comprise channels. The channels may have a width to depth (or height) ratio of 1 to 0.01, wherein the width is a measurement of the width at the narrowest segment of the channel. In some instances, a channel described herein has a width to depth (or height) ratio of 0.5 to 0.01, wherein the width is a measurement of the width at the narrowest segment of the channel. In some instances, a channel described herein has a width to depth (or height) ratio of about 0.01, 0.05, 0.1, 0.15, 0.16, 0.2, 0.5, or 1.

Described herein are structures for polynucleotide sequencing comprising a plurality of discrete loci. Structures comprise, without limitation, substantially planar regions, channels, protrusions, or wells for polynucleotide synthesis. In some instances, structures described herein are provided comprising a plurality of channels, wherein the height or depth of the channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height of a channel is less than 100 um, less than 80 um, less than 60 um, less than 40 um or less than 20 um. In some cases, channel height is about 10, 20, 30, 40, 50, 60, 70, 80, 90, 100, 200, 300, 400, 500 um or more. In some instances, the height or depth of the channel is at least 10, 25, 50, 75, 100, 200, 300, 400, 500, 600, 700, 800, 900, 1000, or more than 1000 nm. In some instances, the height or depth of the channel is in a range of about 10 nm to about 1000 nm, about 25 nm to about 900 nm, about 50 nm to about 800 nm, about 75 nm to about 700 nm, about 100 nm to about 600 nm, or about 200 nm to about 500. Channels described herein may be arranged on a surface in clusters or as a homogenous field.

The width of a locus on the surface of a structure for polynucleotide sequencing described herein may be from about 0.1 um to about 500 um, from about 0.5 um to about 500 um, from about 1 um to about 200 um, from about 1 um to about 100 um, from about 5 um to about 100 um, or from about 0.1 um to about 100 um, for example, about 90 um, 80 um, 70 um, 60 um, 50 um, 40 um, 30 um, 20 um, 10 um, 5 um, 1 um or 0.5 um. In some instances, the width of a locus is less than about 100 um, 90 um, 80 um, 70 um, 60 um, 50 um, 40 um, 30 um, 20 um or 10 um. In some instances, the width of a locus is at least 10, 25, 50, 75, 100, 200, 300, 400, 500, 600, 700, 800, 900, 1000, or more than 1000 nm. In some instances, the width of a locus is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the width of a locus is in a range of about 50 nm to about 1000 nm. In some instances, the distance between the center of two adjacent loci is from about 0.1 um to about 500 um, 0.5 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um. In some instances, the total width of a locus is about 5 um, 10 um, 20 um, 30 um, 40 um, 50 um, 60 um, 70 um, 80 um, 90 um, or 100 um. In some instances, the total width of a locus is about 1 um to 100 um, 30 um to 100 um, or 50 um to 70 um. In some instances, the distance between the center of two adjacent loci is from about 0.5 um to about 2 um, 0.5 um to about 2 um, from about 0.75 um to about 2 um, from about 1 um to about 2 um, from about 0.2 um to about 1 um, from about 0.5 um to about 1.5 um, from about 0.5 um to about 0.8 um, or from about 0.5 um to about 1 um, for example, about 1 um. In some instances, the total width of a locus is about 50 nm, 0.1 um, 0.2 um, 0.3 um, 0.4 um, 0.5 um, 0.6 um, 0.7 um, 0.8 um, 0.9 um, 1 um, 1.1 um, 1.2 um, 1.3 um, 1.4 um, or 1.5 um. In some instances, the total width of a locus is about 0.5 um to 2 um, 0.75 um to 1 um, or 0.9 um to 2 um. In some instances, a locus is substantially planer.

Described herein are structures for polynucleotide sequencing comprising a plurality of discrete loci. Structures comprise, without limitation, substantially planar regions, channels, protrusions, or wells for polynucleotide synthesis. In some instances, structures described herein are provided comprising a plurality of channels, wherein the height or depth of the channel is from about 5 nm to about 500 nm, from about 5 nm to about 400 nm, from about 5 nm to about 300 nm, from about 5 nm to about 200 nm, from about 5 nm to about 100 nm, from about 5 nm to about 50 nm, or from about 10 nm to about 50 nm. In some cases, the height of a channel is less than 100 nm, less than 80 nm, less than 60 nm, less than 40 nm or less than 20 nm. In some cases, channel height is about 10, 20, 30, 40, 50, 60, 70, 80, 90, 100, 200, 300, 400, 500 nm or more. In some instances, the height or depth of the channel is at least 10, 25, 50, 75, 100, 200, 300, 400, 500, 600, 700, 800, 900, 1000, or more than 1000 nm. In some instances, the height or depth of the channel is in a range of about 10 nm to about 1000 nm, about 25 nm to about 900 nm, about 50 nm to about 800 nm, about 75 nm to about 700 nm, about 100 nm to about 600 nm, or about 200 nm to about 500. Channels described herein may be arranged on a surface in clusters or as a homogenous field.

The width of a locus on the surface of a structure for polynucleotide sequencing described herein may be from about 0.1 nm to about 500 nm, from about 0.5 nm to about 500 nm, from about 1 nm to about 200 nm, from about 1 nm to about 100 nm, from about 5 nm to about 100 nm, or from about 0.1 nm to about 100 nm, for example, about 90 nm, 80 nm, 70 nm, 60 nm, 50 nm, 40 nm, 30 nm, 20 nm, 10 nm, 5 nm, 1 nm or 0.5 nm. In some instances, the width of a locus is less than about 100 nm, 90 nm, 80 nm, 70 nm, 60 nm, 50 nm, 40 nm, 30 nm, 20 nm or 10 nm. In some instances, the width of a locus is at least 10, 25, 50, 75, 100, 200, 300, 400, 500, 600, 700, 800, 900, 1000, or more than 1000 nm. In some instances, the width of a locus is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the width of a locus is in a range of about 50 nm to about 1000 nm. In some instances, the distance between the center of two adjacent loci is from about 0.1 nm to about 500 nm, 0.5 nm to about 500 nm, from about 1 nm to about 200 nm, from about 1 nm to about 100 nm, from about 5 nm to about 200 nm, from about 5 nm to about 100 nm, from about 5 nm to about 50 nm, or from about 5 nm to about 30 nm, for example, about 20 nm. In some instances, the total width of a locus is about 5 nm, 10 nm, 20 nm, 30 nm, 40 nm, 50 nm, 60 nm, 70 nm, 80 nm, 90 nm, or 100 nm. In some instances, the total width of a locus is about 1 nm to 100 nm, 30 nm to 100 nm, or 50 nm to 70 nm. In some instances, the distance between the center of two adjacent loci is from about 0.5 nm to about 2 nm, 0.5 nm to about 2 nm, from about 0.75 nm to about 2 nm, from about 1 nm to about 2 nm, from about 0.2 nm to about 1 nm, from about 0.5 nm to about 1.5 nm, from about 0.5 nm to about 0.8 nm, or from about 0.5 nm to about 1 nm, for example, about 1 nm. In some instances, the total width of a locus is about 50 nm, 0.1 nm, 0.2 nm, 0.3 nm, 0.4 nm, 0.5 nm, 0.6 nm, 0.7 nm, 0.8 nm, 0.9 nm, 1 nm, 1.1 nm, 1.2 nm, 1.3 nm, 1.4 nm, or 1.5 nm. In some instances, the total width of a locus is about 0.5 nm to 2 nm, 0.75 nm to 1 nm, or 0.9 nm to 2 nm. In some instances, a locus is substantially planer.

In some instances, each locus supports the sequencing of a population of polynucleotides having a different sequence than a population of polynucleotides being sequenced on another locus. Provided herein are surfaces which comprise at least 10, 100, 256, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In some instances, each cluster includes 109, 121, 130 or 137 loci.

Provided herein are loci having a width at the longest segment of 5 to 100 um. In some cases, the loci have a width at the longest segment of about 30, 35, 40, 45, 50, 55 or 60 um. In some cases, the loci are channels having multiple segments, wherein each segment has a center to center distance apart of 5 to 50 um. In some cases, the center to center distance apart for each segment is about 5, 10, 15, 20 or 25 um.

Provided herein are loci having a width at the longest segment of 5 to 500 nm. In some cases, the loci have a width at the longest segment of about 30, 35, 40, 45, 50, 55, 60, 80, or 100 nm. In some cases, the loci are channels having multiple segments, wherein each segment has a center to center distance apart of 5 to 50 nm. In some cases, the center to center distance apart for each segment is about 5, 10, 15, 20, 25, 50, 100, or 200 nm.

In some instances, the number of distinct polynucleotides sequenced on the surface of a structure described herein is dependent on the number of distinct loci available in the substrate. In some instances, the density of loci is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$,$10^4$ loci per $mm^2$, $10^5$ loci per $mm^2$, $10^6$ loci per $mm^2$, or more. In some cases, a substrate comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some cases, a substrate comprises from about $10^4$ loci per $mm^2$ to about $10^5$ $mm^2$. In some cases, a substrate comprises from about $10^5$ loci per $mm^2$ to about $10^7$ $mm^2$. In some cases, a substrate comprises at least $10^5$ loci per $mm^2$. In some cases, a substrate comprises at least $10^6$ loci per $mm^2$. In some cases, a substrate comprises at least $10^7$ loci per $mm^2$. In some cases, a substrate comprises from about $10^4$ loci per $mm^2$ to about $10^5$ $mm^2$. In some instances, the density of loci is at least or about 1 locus per $um^2$, 10 loci per $um^2$, 25 loci per $um^2$, 50 loci per $um^2$, 65 loci per $um^2$, 75 loci per $um^2$, 100 loci per $um^2$, 130 loci per $um^2$, 150 loci per $um^2$, 175 loci per $um^2$, 200 loci per $um^2$, 300 loci per $um^2$, 400 loci per $um^2$, 500 loci per $um^2$, 1,000 loci per $um^2$ or more. In some cases, a substrate comprises from about 10 loci per $um^2$ to about 500 $um^2$, from about 25 loci per $um^2$ to about 400 $um^2$, from about 50 loci per $um^2$ to about 500 $um^2$, from about 100 loci per $um^2$ to about 500 $um^2$, from about 150 loci per $um^2$ to about 500 $um^2$, from about 10 loci per $um^2$ to about 250 $um^2$, from about 50 loci per $um^2$ to about 250 $um^2$, from about 10 loci per $um^2$ to about 200 $um^2$, or from about 50 loci per $um^2$ to about 200 $um^2$.

In some instances, the distance between the centers of two adjacent loci is from about 10 um to about 500 um, from about 10 um to about 200 um, or from about 10 um to about 100 um. In some cases, the distance between two centers of adjacent loci is greater than about 10 um, 20 um, 30 um, 40 um, 50 um, 60 um, 70 um, 80 um, 90 um or 100 um. In some cases, the distance between the centers of two adjacent loci is less than about 200 um, 150 um, 100 um, 80 um, 70 um, 60 um, 50 um, 40 um, 30 um, 20 um or 10 um. In some cases, the distance between the centers of two adjacent loci is less than about 10000 nm, 8000 nm, 6000 nm, 4000 nm, 2000 nm 1000 nm, 800 nm, 600 nm, 400 nm, 200 nm, 150 nm, 100 nm, 80 um, 70 nm, 60 nm, 50 nm, 40 nm, 30 nm, 20 nm or 10 nm. In some instances, each square meter of a structure described herein allows for at least $10^7$, $10^8$, $10^9$, $10^{10}$, $10^{11}$ loci, where each locus supports one polynucleotide. In some instances, $10^9$ polynucleotides are supported on less than about 6, 5, 4, 3, 2 or 1 $m^2$ of a structure described herein.

In some instances, a structure described herein provides support for the sequencing of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the structure provides support for the sequencing of more than 2,000; 5,000; 10,000; 20,000; 50,000; 100,000; 200,000; 300,000; 00,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence. In some instances, the structure provides a surface environment for the sequence of polynucleotides having at least 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more. In some arrangements, structures for polynucleotide sequencing described herein comprise sites for polynucleotide sequencing in a uniform arrangement. In some instances, the sites for polynucleotide sequencing are in a quasi-uniform arrangement. In some instances, the sites for polynucleotide sequencing are loaded according to a Poisson distribution. In some instances, the sites for polynucleotide sequencing are loaded according to a Normal distribution.

In some instances, polynucleotides are sequenced on distinct loci of a structure, wherein each locus supports the sequencing of a population of polynucleotides. In some cases, each locus supports the sequencing of a population of polynucleotides having a different sequence than a population of polynucleotides sequenced on another locus. In some instances, the loci of a structure are located within a plurality of clusters. In some instances, a structure comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150 or more loci. In some instances, each cluster includes 50 to 500, 100 to 150, or 100 to 200 loci. In some instances, each cluster includes 109, 121, 130 or 137 loci. In some instances, each cluster includes 5, 6, 7, 8, 9, 10, 11 or 12 loci. In some instances, polynucleotides from distinct loci within one cluster have sequences that, when assembled, encode for a contiguous longer polynucleotide of a predetermined sequence.

Structure Size

In some instances, a structure described herein is about the size of a plate (e.g., chip or wafer), for example between about 40 and 120 mm by between about 25 and 100 mm. In some instances, a structure described herein has a diameter less than or equal to about 1000 mm, 500 mm, 450 mm, 400 mm, 300 mm, 250 nm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 84 mm, 76 mm, 54 mm, 51 mm and 25 mm. In some instances, a substrate has a planar surface area of at least 100 $mm^2$; 200 $mm^2$; 500 $mm^2$; 1,000 $mm^2$; 2,000 $mm^2$; 4,500 $mm^2$; 5,000 $mm^2$; 10,000 $mm^2$; 12,000 $mm^2$; 15,000 $mm^2$; 20,000 $mm^2$; 30,000 $mm^2$; 40,000 $mm^2$; 50,000 $mm^2$ or more. In some instances, the thickness is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples thickness include 275 mm, 375 mm, 525 mm, 625 mm, 675 mm, 725 mm, 775 mm and 925 mm. In some instances, the thickness is at least or about 0.5 mm, 1.0 mm, 1.5 mm, 2.0 mm, 2.5 mm, 3.0 mm, 3.5 mm, 4.0 mm, or more than 4.0 mm. In some cases, the thickness of varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension. In some instances, a structure comprises an array of polynucleotide synthesis devices. In some instances, a structure is integrated into a CMOS.

Materials

Provided herein are devices comprising a surface, wherein the surface is modified to support polynucleotide sequencing at predetermined locations and with a resulting low error rate, a low dropout rate, a high yield, and a high oligo representation. In some instances, surfaces of devices for polynucleotide sequencing provided herein are fabricated from a variety of materials capable of modification to support a de novo polynucleotide sequencing reaction. In some cases, the devices are sufficiently conductive, e.g., are able to form uniform electric fields across all or a portion of the devices. Devices described herein may comprise a flexible material. Exemplary flexible materials include, without limitation, modified nylon, unmodified nylon, nitrocellulose, and polypropylene. Devices described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Devices disclosed herein may be fabricated from a material comprising silicon, polystyrene, agarose, dextran, cellulosic polymers, polyacrylamides, polydimethylsiloxane (PDMS), glass, or any combination thereof. In some cases, devices disclosed herein are manufactured with a combination of materials listed herein or any other suitable material known in the art.

Devices described herein may comprise material having a range of tensile strength. Exemplary materials having a range of tensile strengths include, but are not limited to, nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide sequencing that is in the form of a flexible material capable of being stored in a continuous loop or reel, such as a tape or flexible sheet.

Young's modulus measures the resistance of a material to elastic (recoverable) deformation under load. Exemplary materials having a range of Young's modulus stiffness include, but are not limited to, nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load. In some instances, a solid support described herein has a surface with a flexibility of at least nylon.

In some cases, devices disclosed herein comprise a silicon dioxide base and a surface layer of silicon oxide. Alternatively, the devices may have a base of silicon oxide. Surface of the devices provided here may be textured, resulting in an increase overall surface area for polynucleotide synthesis. Devices disclosed herein in some instances comprise at least 5%, 10%, 25%, 50%, 80%, 90%, 95%, or 99% silicon. Devices disclosed herein in some instances are fabricated from silicon on insulator (SOI) wafer.

The structure may be fabricated from a variety of materials, suitable for the methods and compositions of the invention described herein. In instances, the materials from which the substrates/solid supports of the comprising the invention are fabricated exhibit a low level of polynucleotide binding. In some situations, material that are transparent to visible and/or UV light can be employed. Materials that are sufficiently conductive, e.g. those that can form uniform electric fields across all or a portion of the substrates/solids support described herein, can be utilized. In some instances, such materials may be connected to an electric ground. In some cases, the substrate or solid support can be heat conductive or insulated. The materials can be chemical resistant and heat resistant to support chemical or biochemical reactions such as a series of polynucleotide sequencing reactions. For flexible materials, materials of interest can include: nylon, both modified and unmodified, nitrocellulose, polypropylene, and the like.

For rigid materials, specific materials of interest include: glass; fuse silica; silicon, plastics (for example polytetrafluoroethylene, polypropylene, polystyrene, polycarbonate, and blends thereof, and the like); metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some cases, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as a polynucleotide sequencing reaction. In some instances, the substrate is magnetic. In some instances, the structures comprise a metal or a metal alloy.

Structures for polynucleotide sequencings may be over 1, 2, 5, 10, 30, 50 or more feet long in any dimension. In the case of a flexible structure, the flexible structure is optionally stored in a wound state, e.g., in a reel. In the case of a large rigid structure, e.g., greater than 1 foot in length, the rigid structure can be stored vertically or horizontally.

Surface Preparation

In some instances, a surface of a structure disclosed herein is modified to comprise one or more actively functionalized surfaces configured to bind to both the surface of the substrate and a biomolecule (e.g., polynucleotide, polymerase, primer, or a complex of any combination thereof), thereby supporting a coupling reaction to the surface. In some instances, the surface is also functionalized with a passive material that does not efficiently bind the biomolecule, thereby preventing biomolecule attachment at sites where the passive functionalization agent is bound. In some cases, the surface comprises an active layer only defining distinct loci for biomolecule support.

In some instances, the surface is contacted with a mixture of functionalization groups which are in any different ratio. In some instances, a mixture comprises at least 2, 3, 4, 5 or more different types of functionalization agents. In some cases, the ratio of the at least two types of surface functionalization agents in a mixture is about 1:1, 1:2, 1:5, 1:10, 2:10, 3:10, 4:10, 5:10, 6:10, 7:10, 8:10, 9:10, or any other ratio to achieve a desired surface representation of two groups. In some instances, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some instances, the mixture of functionalization reagents comprises one or more reagents that bind to a biomolecule and one or more reagents that do not bind to a biomolecule. Therefore, modulation of the reagents allows for the control of the amount of biomolecule binding that occurs at a distinct area of functionalization. In some instances, the amount of biomolecule binding may be about 10%, 20%, 30%, 40%, 50%, 60%, or 70% of the binding capacity of the structure. In some instances, the amount of biomolecule binding may be about 10 to 60%, about 10 to 50%, about 20 to 50%, or about 20 to 40% of the binding capacity of the structure.

In some instances, a method for substrate functionalization comprises deposition of a silane molecule onto a surface of a substrate. The silane molecule may be deposited on a high energy surface of the substrate. In some instances, the high surface energy region includes a passive functionalization reagent. Methods described herein provide for a silane group to bind the surface, while the rest of the molecule provides a distance from the surface and a free hydroxyl group at the end to which a biomolecule attaches. In some instances, the silane is an organofunctional alkoxysilane molecule. Non-limiting examples of organofunctional alkoxysilane molecules include dimethylchloro-octodecyl-silane, methyldichloro-octodecyl-silane, trichloro-octodecyl-silane, and trimethyl-octodecyl-silane, triethyl-octodecyl-silane. In some instances, the silane is an amino silane. Examples of amino silanes include, without limitation, 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances, the silane comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane, N-(3-triethoxysilylpropyl)-4-hydroxybutyramide, or any combination thereof. In some instances, an active functionalization agent comprises 11-acetoxyundecyltriethoxysilane. In some instances, an active functionalization agent comprises n-decyltriethoxysilane. In some cases, an active functionalization agent comprises glycidyloxypropyltriethoxysilane (GOPS). In some instances, the silane is a fluorosilane. In some instances, the silane is a hydrocarbon silane. In some cases, the silane is 3-iodo-propyltrimethoxysilane. In some cases, the silane is octylchlorosilane.

In some instances, silanization is performed on a surface through self-assembly with organofunctional alkoxysilane molecules. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). In some cases, the dimeric secondary aminoalkyl siloxanes is bis (3-trimethoxysilylpropyl) amine turning into bis(silyloxylpropyl)amine.

Active functionalization areas may comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane. In some instances, an active functionalization agent comprises 11-acetoxyundecyltriethoxysilane and n-decyltriethoxysilane in a ratio from about 20:80 to about 1:99, or about 10:90 to about 2:98, or about 5:95.

In some instances, functionalization comprises deposition of a functionalization agent to a structure by any deposition technique, including, but not limiting to, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD), physical vapor deposition (e.g., sputter deposition, evaporative deposition), and molecular layer deposition (MLD).

Any step or component in the following functionalization process be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a surface of a structure is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for surface functionalization optionally comprises a resist coat and a resist strip. In some instances, following active surface functionalization, the substrate is spin coated with a resist, for example, SPR™ 3612 positive photoresist. The process for surface functionalization, in various instances, comprises lithography with patterned functionalization. In some instances, photolithography is performed following resist coating. In some instances, after lithography, the surface is visually inspected for lithography defects. The process for surface functionalization, in some instances, comprises a cleaning step, whereby residues of the substrate are removed, for example, by plasma cleaning or etching. In some instances, the plasma cleaning step is performed at some step after the lithography step.

In some instances, a surface coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In some instances, the methods and compositions described herein relate to the application of photoresist for the generation of modified surface properties in selective areas, wherein the application of the photoresist relies on the fluidic properties of the surface defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Structures may be designed to control the flow of fluids by facilitating or inhibiting wicking effects into neighboring fluidic paths. For example, a structure is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

In some instances, a structure described herein has a surface that comprises a material having thickness of at least or at least 0.1 nm, 0.5 nm, 1 nm, 2 nm, 5 nm, 10 nm or 25 nm that comprises a reactive group capable of binding nucleosides. Exemplary include, without limitation, glass and silicon, such as silicon dioxide and silicon nitride. In some cases, exemplary surfaces include nylon and PMMA.

In some instances, electromagnetic radiation in the form of UV light is used for surface patterning. In some instances, a lamp is used for surface patterning, and a mask mediates exposure locations of the UV light to the surface. In some instances, a laser is used for surface patterning, and a shutter opened/closed state controls exposure of the UV light to the surface. The laser arrangement may be used in combination with a flexible structure that is capable of moving. In such an arrangement, the coordination of laser exposure and flexible structure movement is used to create patterns of one or more agents having differing nucleoside coupling capabilities.

Material Deposition Systems

In some cases, the sequenced polynucleotides are stored on the substrate, for example a solid support. Polynucleotides may be deposited on a substrate surface in a non-continuous, or drop-on-demand method. In some instances, polynucleotides are transferred to a device for sequencing. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some cases, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some cases, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl.

In some arrangements, the configuration of a polynucleotide sequencing system allows for a continuous polynucleotide sequencing process that exploits the flexibility of a substrate for traveling in a reel-to-reel type process. This sequencing process operates in a continuous production line manner with the substrate travelling through various stages of polynucleotide sequencing using one or more reels to rotate the position of the substrate. In an exemplary instance, a reaction in polynucleotide sequencing comprises rolling a substrate: through a solvent bath, beneath a deposition device for phosphoramidite deposition, through a bath of oxidizing agent, through an acetonitrile wash bath, and through a deblock bath. Optionally, the tape is also traversed through a capping bath. A reel-to-reel type process allows for the finished product of a substrate comprising sequenced polynucleotides to be easily gathered on a take-up reel, where it can be transported for further processing or storage.

Described herein are devices, methods, systems and compositions where reagents for polynucleotide sequencing are recycled or reused. Recycling of reagents may comprise collection, storage, and usage of unused reagents, or purification/transformation of used reagents. For example, a reagent bath is recycled and used for a polynucleotide sequencing step on the same or a different surface. Reagents described herein may be recycled 1, 2, 3, 4, 5, 6, 7, 8, 9, 10 or more times. Alternatively, or in combination, a reagent solution comprising a reaction byproduct is filtered to remove the byproduct, and the reagent solution is used for additional polynucleotide sequencing reactions.

Many integrated or non-integrated elements are often used with polynucleotide sequencing systems. In some instances, a polynucleotide sequencing system comprises one or more elements useful for processing of synthesized polynucleotides before they are sequenced. As an example, the system comprises a temperature control element such as a thermal cycling device. In some instances, the temperature control element is used with a plurality of resolved reactors to perform nucleic acid assembly such as PCA and/or nucleic acid amplification such as PCR, prior to polynucleotide sequencing.

De Novo Polynucleotide Synthesis

Provided herein are systems and methods for synthesis of a high density of polynucleotides on a substrate in a short amount of time. In some instances, the substrate is a flexible substrate. In some instances, at least $10^{10}$, $10^{11}$, $10^{12}$, $10^{13}$, $10^{14}$, or $10^{15}$ bases are synthesized in one day. In some instances, at least $10\times10^{8}$, $10\times10^{9}$, $10\times10^{10}$, $10\times10^{11}$, or $10\times10^{12}$ polynucleotides are synthesized in one day. In some cases, each polynucleotide synthesized comprises at least 20, 50, 100, 200, 300, 400 or 500 nucleobases. In some cases, these bases are synthesized with a total average error rate of less than about 1 in 100; 200; 300; 400; 500; 1000; 2000; 5000; 10000; 15000; 20000 bases. In some instances, these error rates are for at least 50%, 60%, 70%, 80%, 90%, 95%, 98%, 99%, 99.5%, or more of the polynucleotides synthesized. In some instances, these at least 90%, 95%, 98%, 99%, 99.5%, or more of the polynucleotides synthesized do not differ from a predetermined sequence for which they encode. In some instances, the error rate for synthesized polynucleotides on a substrate using the methods and systems described herein is less than about 1 in 200. In some instances, the error rate for synthesized polynucleotides on a substrate using the methods and systems described herein is less than about 1 in 1,000. In some instances, the error rate for synthesized polynucleotides on a substrate using the methods and systems described herein is less than about 1 in 2,000. In some instances, the error rate for synthesized polynucleotides on a substrate using the methods and systems described herein is less than about 1 in 3,000. In some instances, the error rate for synthesized polynucleotides on a substrate using the methods and systems described herein is less than about 1 in 5,000. Individual types of error rates include mismatches, deletions, insertions, and/or substitutions for the polynucleotides synthesized on the substrate. The term "error rate" refers to a comparison of the collective amount of synthesized polynucleotide to an aggregate of predetermined polynucleotide sequences. In some instances, synthesized polynucleotides disclosed herein comprise a tether of 12 to 25 bases. In some instances, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

Described herein are methods, systems, devices, and compositions wherein chemical reactions used in polynucleotide synthesis are controlled using electrochemistry. Electrochemical reactions in some instances are controlled by any source of energy, such as light, heat, radiation, or electricity. For example, electrodes are used to control chemical reactions as all or a portion of discrete loci on a surface. Electrodes in some instances are charged by applying an electrical potential to the electrode to control one or more chemical steps in polynucleotide synthesis. In some instances, these electrodes are addressable. Any number of the chemical steps described herein is in some instances controlled with one or more electrodes. Electrochemical reactions may comprise oxidations, reductions, acid/base chemistry, or other reaction that is controlled by an electrode. In some instances, electrodes generate electrons or protons that are used as reagents for chemical transformations. Electrodes in some instances directly generate a reagent such as an acid. In some instances, an acid is a proton. Electrodes in some instances directly generate a reagent such as a base. Acids or bases are often used to cleave protecting groups, or influence the kinetics of various polynucleotide synthesis reactions, for example by adjusting the pH of a reaction solution. Electrochemically controlled polynucleotide synthesis reactions in some instances comprise redox-active metals or other redox-active organic materials. In some instances, metal or organic catalysts are employed with these electrochemical reactions. In some instances, acids are generated from oxidation of quinones.

Control of chemical reactions with is not limited to the electrochemical generation of reagents; chemical reactivity may be influenced indirectly through biophysical changes to substrates or reagents through electric fields (or gradients) which are generated by electrodes. In some instances, substrates include but are not limited to nucleic acids. In some instances, electrical fields which repel or attract specific reagents or substrates towards or away from an electrode or surface are generated. Such fields in some instances are generated by application of an electrical potential to one or more electrodes. For example, negatively charged nucleic acids are repelled from negatively charged electrode surfaces. Such repulsions or attractions of polynucleotides or other reagents caused by local electric fields in some instances provides for movement of polynucleotides or other reagents in or out of region of the synthesis device or structure. In some instances, electrodes generate electric fields which repel polynucleotides away from a synthesis surface, structure, or device. In some instances, electrodes generate electric fields which attract polynucleotides towards a synthesis surface, structure, or device. In some instances, protons are repelled from a positively charged surface to limit contact of protons with substrates or portions thereof. In some instances, repulsion or attractive forces are used to allow or block entry of reagents or substrates to specific areas of the synthesis surface. In some instances, nucleoside monomers are prevented from contacting a polynucleotide by application of an electric field in the vicinity of one or both components. Such arrangements allow gating of specific reagents, which may obviate the need for protecting groups when the concentration or rate of contact between reagents and/or substrates is controlled. In some instances, unprotected nucleoside monomers are used for polynucleotide synthesis. Alternatively, application of the field in the vicinity of one or both components promotes contact of nucleoside monomers with a polynucleotide. Additionally, application of electric fields to a substrate can alter the substrates reactivity or conformation. In an exemplary application, electric fields generated by electrodes are used to prevent polynucleotides at adjacent loci from interacting. In some instances, the substrate is a polynucleotide, optionally attached to a surface. Application of an electric field in some instances alters the three-dimensional structure of a polynucleotide. Such alterations comprise folding or unfolding of various structures, such as helices, hairpins, loops, or other 3-dimensional nucleic acid structure. Such alterations are useful for manipulating nucleic acids inside of wells, channels, or other structures. In some instances, electric fields are applied to a nucleic acid substrate to prevent secondary structures. In some instances, electric fields obviate the need for linkers or attachment to a solid support during polynucleotide synthesis.

A suitable method for polynucleotide synthesis on a substrate of this disclosure is a phosphoramidite method comprising the controlled addition of a phosphoramidite building block, e.g. nucleoside phosphoramidite, to a growing polynucleotide in a coupling step that forms a phosphite triester linkage between the phosphoramidite building block and a nucleoside bound to the substrate. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is de-protected by removal of a protecting group, where the protecting group functions to prevent polymerization. Protecting groups may comprise any chemical group that prevents extension of the polynucleotide. In some instances, the protecting group is cleaved (or removed) in the presence of an acid. In some instances, the protecting group is cleaved in the presence of a base. In some instances, the protecting group is removed with electromagnetic radiation such as light, heat, or other energy source. In some instances, the protecting group is removed through an oxidation or reduction reaction. In some instances, a protecting group comprises a triarylmethyl group. In some instances, a protecting group comprises an aryl ether. In some instances, a protecting comprises a disulfide. In some instances, a protecting group comprises an acid-labile silane. In some instances, a protecting group comprises an acetal. In some instances, a protecting group comprises a ketal. In some instances, a protecting group comprises an enol ether. In some instances, a protecting group comprises a methoxybenzyl group. In some instances, a protecting group comprises an azide. In some instances, a protecting group is 4,4'-dimethoxytrityl (DMT). In some instances, a protecting group is a tert-butyl carbonate. In some instances, a protecting group is a tert-butyl ester. In some instances, a protecting group comprises a base-labile group. In some instances, enzymatic methods are used to generate polynucleotides. In some instances, enzymatic methods comprise use of polymerases. In some instances, enzymatic methods comprise use of protected nucleotides. In some instances, enzymatic methods comprise use a terminal deoxytransferase, or variant there.

Following coupling, phosphoramidite polynucleotide synthesis methods optionally comprise a capping step. In a capping step, the growing polynucleotide is treated with a capping agent. A capping step generally serves to block unreacted substrate-bound 5'-OH groups after coupling from further chain elongation, preventing the formation of polynucleotides with internal base deletions. Further, phosphoramidites activated with 1H-tetrazole often react, to a small extent, with the O6 position of guanosine. Without being bound by theory, upon oxidation with $I_2$/water, this side product, possibly via O6-N7 migration, undergoes depurination. The apurinic sites can end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

Following addition of a nucleoside phosphoramidite, and optionally after capping and one or more wash steps, a substrate described herein comprises a bound growing nucleic acid that may be oxidized. The oxidation step comprises oxidizing the phosphite triester into a tetracoordinated phosphate triester, a protected precursor of the naturally occurring phosphate diester internucleoside linkage. In some instances, phosphite triesters are oxidized electrochemically. In some instances, oxidation of the growing polynucleotide is achieved by treatment with iodine and water, optionally in the presence of a weak base such as a pyridine, lutidine, or collidine. Oxidation is sometimes carried out under anhydrous conditions using tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

For a subsequent cycle of nucleoside incorporation to occur through coupling, a protected 5' end (or 3' end, if synthesis is conducted in a 5' to 3' direction) of the substrate bound growing polynucleotide is be removed so that the primary hydroxyl group can react with a next nucleoside phosphoramidite. In some instances, the protecting group is DMT and deblocking occurs with trichloroacetic acid in dichloromethane. In some instances, the protecting group is DMT and deblocking occurs with electrochemically generated protons. Conducting detritylation for an extended time or with stronger than recommended solutions of acids may lead to increased depurination of solid support-bound polynucleotide and thus reduces the yield of the desired full-length product. Methods and compositions described herein provide for controlled deblocking conditions limiting undesired depurination reactions. In some instances, the substrate bound polynucleotide is washed after deblocking. In some cases, efficient washing after deblocking contributes to synthesized polynucleotides having a low error rate.

Methods for the synthesis of polynucleotides on a substrate described herein may involve an iterating sequence of the following steps: application of a protected monomer to a surface of a substrate feature to link with either the surface, a linker or with a previously deprotected monomer; deprotection of the applied monomer so that it can react with a subsequently applied protected monomer; and application of another protected monomer for linking. One or more intermediate steps include oxidation and/or sulfurization. In some instances, one or more wash steps precede or follow one or all of the steps.

Methods for the synthesis of polynucleotides on a substrate described herein may comprise an oxidation step. For example, methods involve an iterating sequence of the following steps: application of a protected monomer to a surface of a substrate feature to link with either the surface, a linker or with a previously deprotected monomer; deprotection of the applied monomer so that it can react with a subsequently applied protected monomer; application of another protected monomer for linking, and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

In some instances, polynucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied, and the surface can be exposed to UV light to generate second pattern of hydroxyl groups, followed by coupling with 5'-photoprotected nucleoside phosphoramidite. Likewise, patterns can be generated, and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of a substrate described herein that provides support for polynucleotide synthesis may be chemically modified to allow for the synthesized polynucleotide to be cleaved from the surface. In some instances, the polynucleotide is cleaved at the same time as the polynucleotide is deprotected. In some cases, the polynucleotide is cleaved after the polynucleotide is deprotected. In an exemplary scheme, a trialkoxysilyl amine such as $(CH_3CH_2O)_3Si—(CH_2)_2—NH_2$ is reacted with surface SiOH groups of a substrate, followed by reaction with succinic anhydride with the amine to create an amide linkage and a free OH on which the nucleic acid chain growth is supported. Cleavage includes gas cleavage with ammonia or methylamine. In some instances, cleavage includes linker cleavage with electrically generated reagents such as acids or bases. In some instances, once released from the surface, polynucleotides are assembled into larger nucleic acids that are sequenced and decoded to extract stored information.

The surfaces described herein can be reused after polynucleotide cleavage to support additional cycles of polynucleotide synthesis. For example, the linker can be reused without additional treatment/chemical modifications. In some instances, a linker is non-covalently bound to a substrate surface or a polynucleotide. In some embodiments, the linker remains attached to the polynucleotide after cleavage from the surface. Linkers in some embodiments comprise reversible covalent bonds such as esters, amides, ketals, beta substituted ketones, heterocycles, or other group that is capable of being reversibly cleaved. Such reversible cleavage reactions are in some instances controlled through the addition or removal of reagents, or by electrochemical processes controlled by electrodes. Optionally, chemical linkers or surface-bound chemical groups are regenerated after a number of cycles, to restore reactivity and remove unwanted side product formation on such linkers or surface-bound chemical groups.

Computer Systems

In various aspects, any of the systems described herein are operably linked to a computer and are optionally automated through a computer either locally or remotely. In various instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. In some instances, the computer systems are programmed to interface between the user specified base sequence and the position of a material deposition device to deliver the correct reagents to specified regions of the substrate. As an example, a computer system, such as the system shown in FIG. 6 or FIG. 7, may be used for encoding data represented as a set of symbols to another set of symbols. For example, the data may be represented as numerical symbols, such as binary values of "0"s and "1"s and the computer system may execute a computer program to convert the data to a plurality of nucleic acid sequences, convert a plurality of nucleic acid sequences to data, or both. In some examples, a computer program may be a machine learning algorithm. In some examples, the machine learning algorithm may determine a nucleotide base based on an electrical signal, such as current or voltage.

Figure 6:
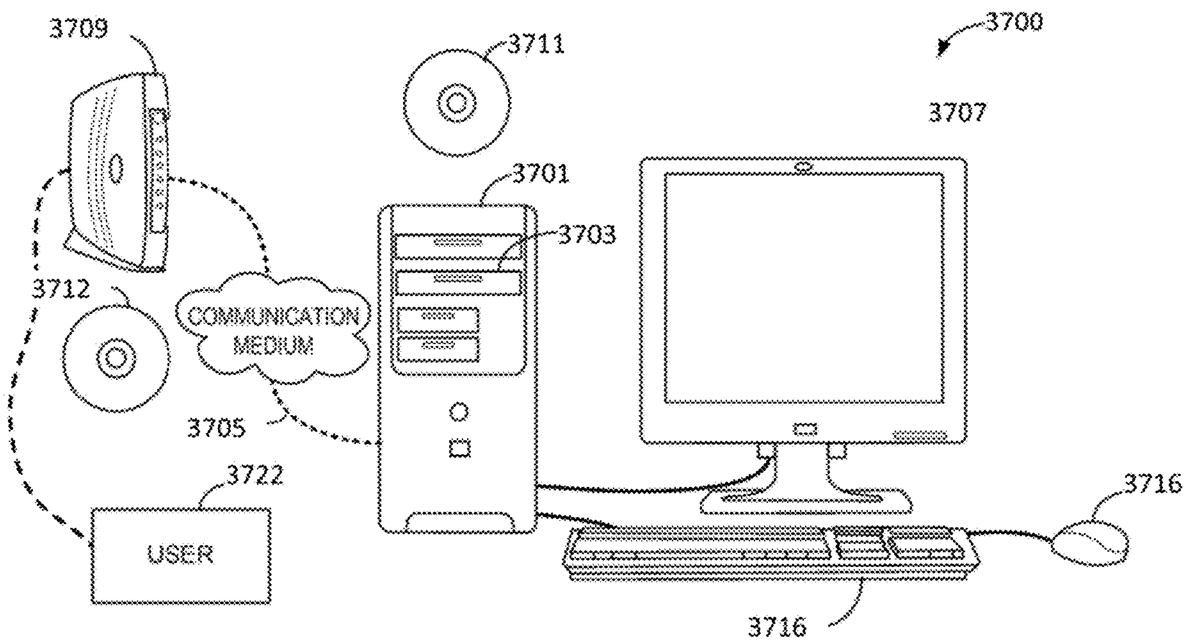
FIG. 6 illustrates an example of a computer system.

The computer system 3700 illustrated in FIG. 6 may be understood as a logical apparatus that can read instructions from media 3711 and/or a network port 3705, which can optionally be connected to server 3709 having fixed media 3712. The system can include a CPU 3701, disk drives 3703, optional input devices such as keyboard 3715 and/or mouse 3716 and optional monitor 3707. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 3722.

Figure 5:
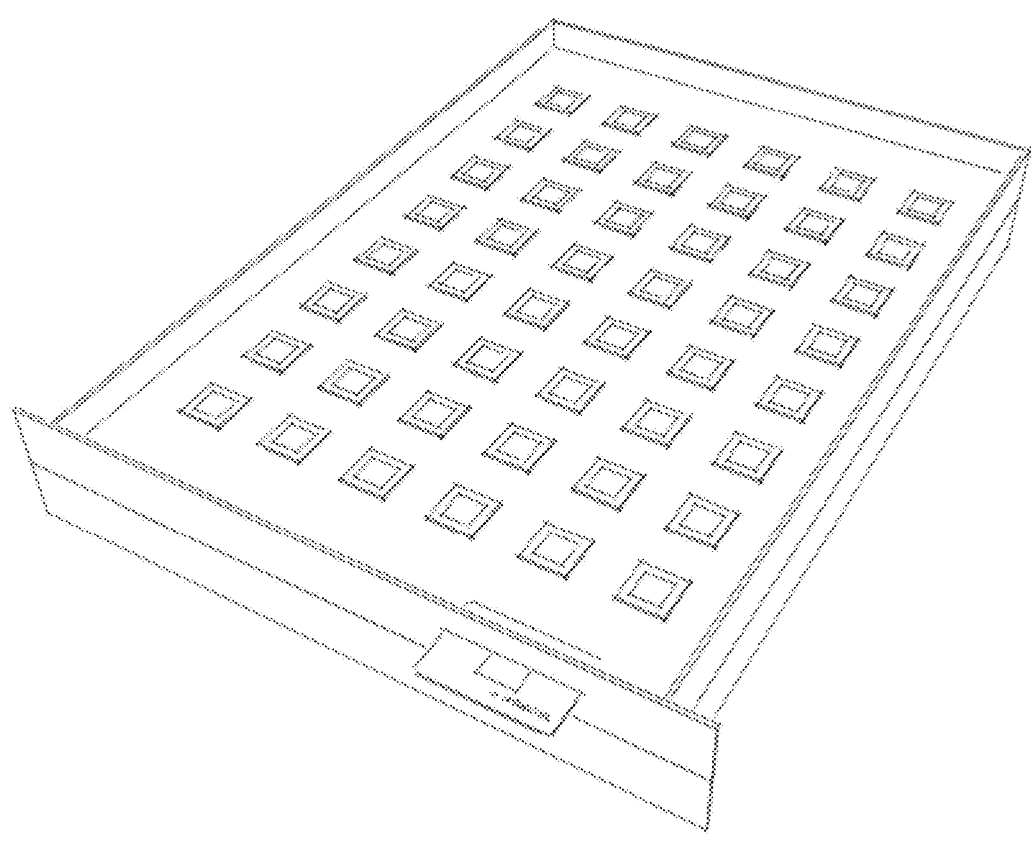
FIG. 5 is an example of rack-style instrument. Such instruments may comprise hundreds or thousands of solid support arrays.
Figure 7:
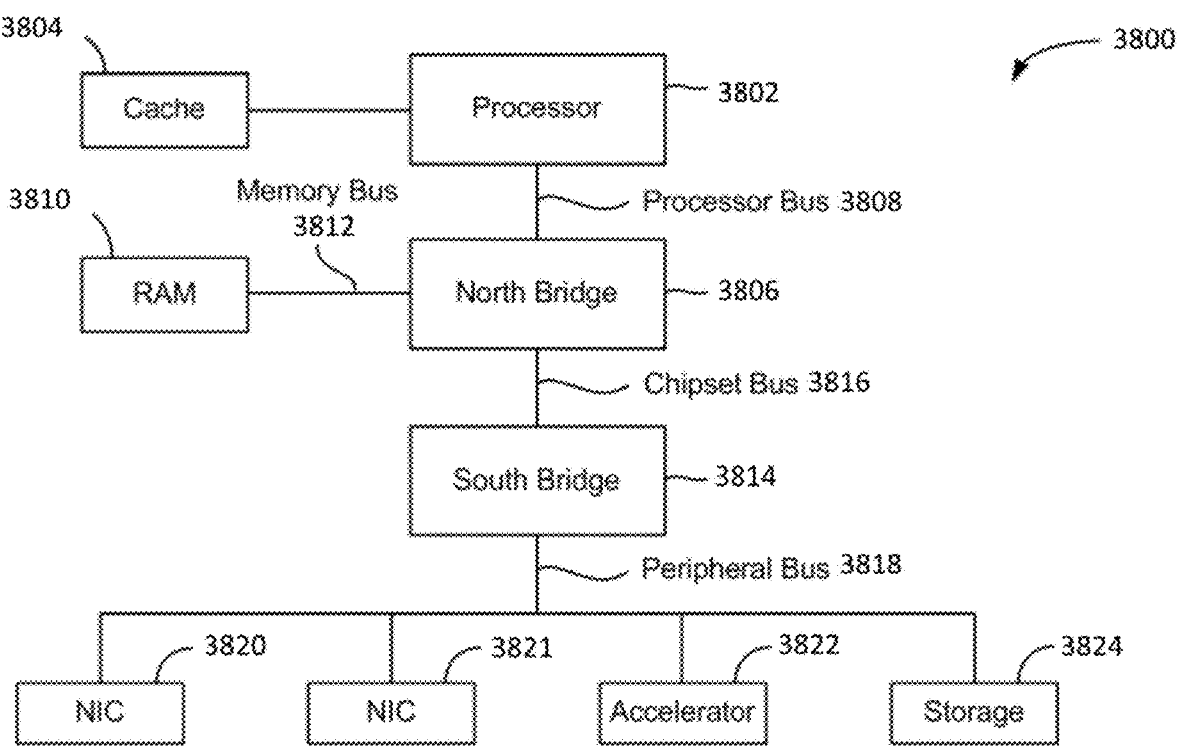
FIG. 7 is a block diagram illustrating architecture of a computer system.

FIG. 7 is a block diagram illustrating a first example architecture of a computer system that can be used in connection with example instances of the present invention. As depicted in FIG. 5, the example computer system can include a processor 3802 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices. As illustrated in FIG. 38, a high speed cache 3804 can be connected to, or incorporated in, the processor 3802 to provide a high speed memory for instructions or data that have been recently, or are frequently, used by processor 3802. The processor 3802 is connected to a north bridge 3806 by a processor bus 3808. The north bridge 3806 is connected to random access memory (RAM) 3810 by a memory bus 3812 and manages access to the RAM 3810 by the processor 3802. The north bridge 3806 is also connected to a south bridge 3814 by a chipset bus 3816. The south bridge 3814 is, in turn, connected to a peripheral bus 3818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 3818. In some alternative architectures, the functionality of the north bridge can be incorporated into the processor instead of using a separate north bridge chip. In some instances, a system 3800 can include an accelerator card 3822 attached to the peripheral bus 3818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 3824 and can be loaded into RAM 3810 and/or cache 3804 for use by the processor. The system 3800 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 3800 also includes network interface cards (NICs) 3820 and 3821 connected to the peripheral bus for providing network interfaces to external storage, such as Network Attached Storage (NAS) and other computer systems that can be used for distributed parallel processing.

Figure 8:
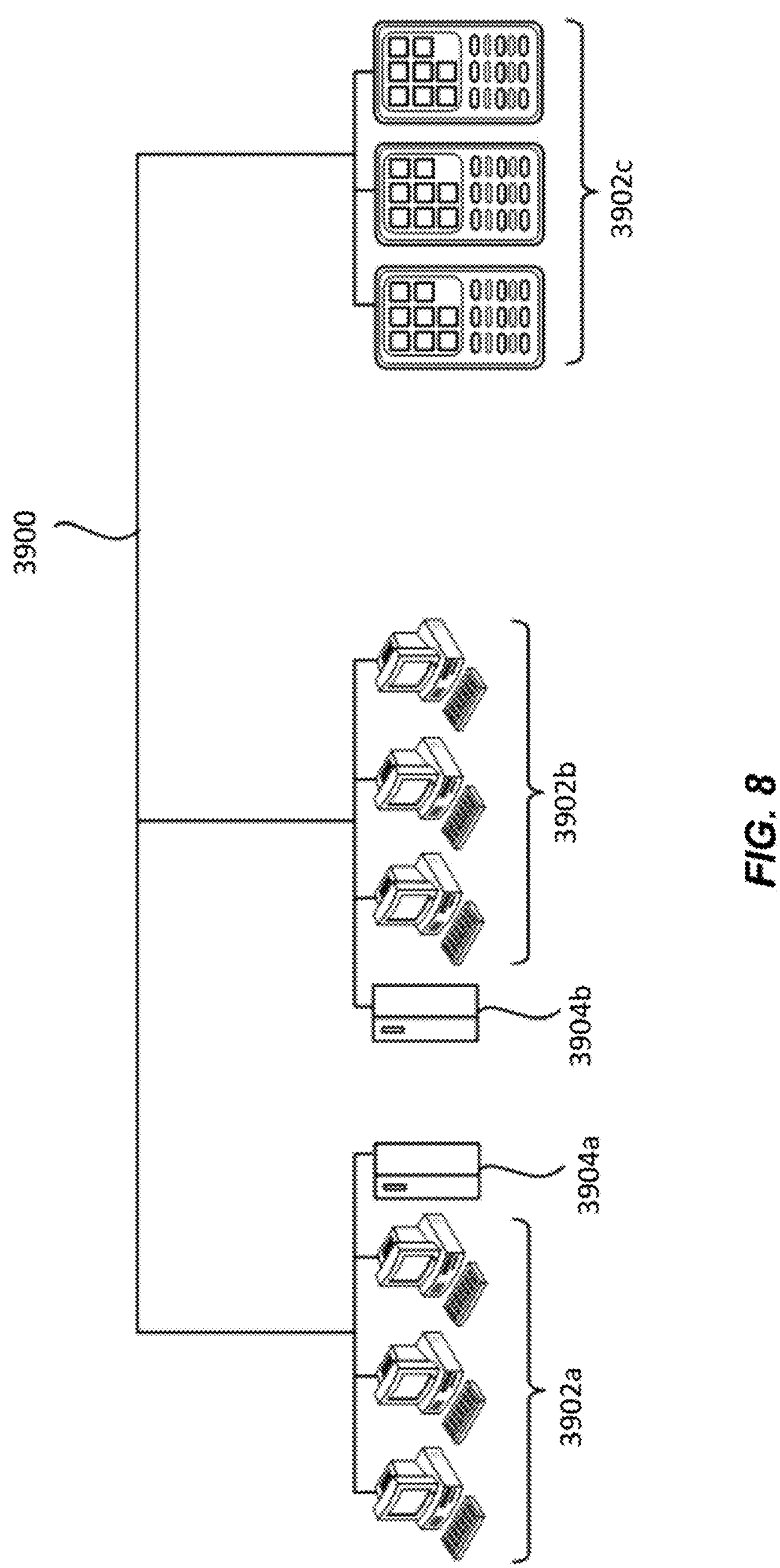
FIG. 8 is a diagram demonstrating a network configured to incorporate a plurality of computer systems, a plurality of cell phones and personal data assistants, and Network Attached Storage (NAS).

FIG. 8 is a diagram showing a network 3900 with a plurality of computer systems 3902*a*, and 3902*b*, a plurality of cell phones and personal data assistants 3902*c*, and Network Attached Storage (NAS) 3904*a*, and 3904*b*. In example embodiments, systems 3902*a*, 3902*b*, and 3902*c* can manage data storage and optimize data access for data stored in Network Attached Storage (NAS) 3904*a* and 3904*b*. A mathematical model can be used for the data and be evaluated using distributed parallel processing across computer systems 3902*a*, and 3902*b*, and cell phone and personal data assistant systems 3902*c*. Computer systems 3902*a*, and 3902*b*, and cell phone and personal data assistant systems 3902*c* can also provide parallel processing for adaptive data restructuring of the data stored in Network Attached Storage (NAS) 3904*a* and 3904*b*. FIG. 39 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

Figure 9:
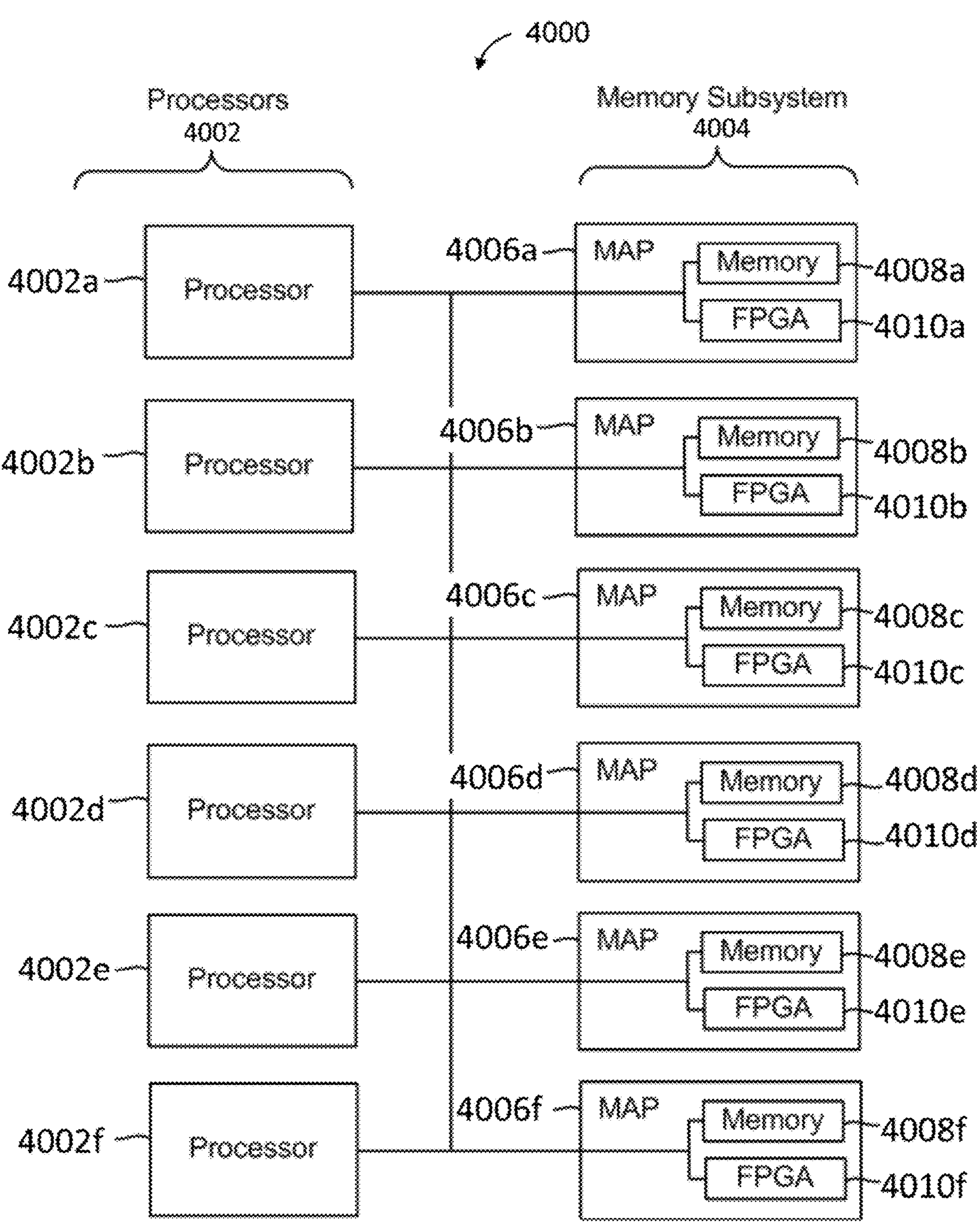
FIG. 9 is a block diagram of a multiprocessor computer system using a shared virtual address memory space.

In some example embodiments, processors can maintain separate memory spaces and transmit data through network interfaces, back plane or other connectors for parallel processing by other processors. In other embodiments, some or all of the processors can use a shared virtual address memory space. FIG. 9 is a block diagram of a multiprocessor computer system 4000 using a shared virtual address memory space in accordance with an example embodiment. The system includes a plurality of processors 4002*a-f* that can access a shared memory subsystem 4004. The system incorporates a plurality of programmable hardware memory algorithm processors (MAPs) 4006*a-f* in the memory subsystem 4004. Each MAP 4006*a-f* can comprise a memory 4008*a-f* and one or more field programmable gate arrays (FPGAs) 4010*a-f*. The MAP provides a configurable functional unit and particular algorithms or portions of algorithms can be provided to the FPGAs 4010*a-f* for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 4008*a-f*, allowing it to execute tasks independently of, and asynchronously from, the respective microprocessor 4002*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card.

EXAMPLES

Example 1

Polynucleotides are sequenced using fluorophore nucleotides. Prior to sequencing, polynucleotides are synthesized (or otherwise obtained) and prepared according to the general scheme in FIG. 1, resulting in a plurality of ternary complexes comprising the polynucleotide, primer, and polymerase. Polynucleotide ternary complexes libraries comprising the plurality of ternary complexes are created and loaded on a single molecule sequencing chip comprising loci.

Each of the ternary complexes are loaded on a locus of the single molecule sequencing chip. Each of the polynucleotides in the ternary complexes is attached to a locus of the sequencing chip using avidin/biotin linkages in order to tether the ternary complex to the sequencing chip. The ternary complexes are loaded on the sequencing chip according to a Poisson distribution at approximately 33% capacity of the sequencing chip.

A reaction mixture is prepared, comprising free nucleotides, A, T, C, and G, which are each labeled with a unique fluorophore. In this case, unique fluorophores are attached to the nucleotides through a phosphoramidate linkage at the terminal phosphate of the nucleotides.

During sequencing, nucleotides with unique fluorophores are consecutively incorporated into the sequence of polynucleotides via the polymerase and a primer. Excitation sources are configured to release one or more excitation energies with appropriate wavelengths for exciting each of the unique fluorophores. The excitation energies released by the excitation sources are pulsed at predetermined time intervals and the fluorescence lifetimes of the fluorophores are measured. The fluorescence lifetime measurements are used to determine the newly incorporated nucleotide. Following the detection of the newly incorporated nucleotide, the phosphoramidate linkage is cleaved using a polymerase in order to separate the fluorophore from the polynucleotide. The sequence obtained from the collection of detected emissions is then used to determine the sequence of the polynucleotide via sequence complementarity. Following the sequencing of the polynucleotides loaded on the sequencing chip, the avidin/biotin linkages are cleaved during a washing step to separate the ternary complexes from the sequencing chip. The avidin/biotin linkages are disrupted by washing the sequencing chip with an eluent comprising biotin, thereby releasing the ternary complex from the surface of the sequencing chip.

After removing the ternary complexes, optionally the surface of the sequencing chip is reconditioned for reuse. A new ternary complex library is then reloaded on the sequencing chip for sequencing, and the sequencing steps as described herein are repeated.

Example 2

Electronics are used to sequence polynucleotides. Polynucleotides are synthesized and loaded on a sequencing chip according to the general methods of Example 1.

The sequencing chip comprises a molecular electronic sensor comprising a pair of electrodes that are spaced apart. A molecular complex is attached to each electrode to form a molecular electronics circuit. The molecular complex comprises a carbon nanotube bridge and a polymerase probe molecule that modulates a measurable electrical parameter through its activity.

A current is run through the electrodes and through the molecular complex to produce distinguishable signals depending on the patterns of the nucleotide being incorporated in the sequence. The distinguishable measured electrical parameters are converted into binary data, which are related to the polynucleotide sequence.

After the polynucleotides in the ternary complexes are sequenced, the sequencing chip is washed, and the ternary complexes are removed from the sequencing chip according to the general method of Example 1. The sequencing chip is then prepared for reuse and are reloaded with a new ternary complex library.

Example 3

Polynucleotide sequencing using nanopore sequencing by synthesis (SBS) is conducted. Polynucleotides are sequenced and loaded on a sequencing chip according to the general methods of Example 1.

The sequencing device comprises nanopores that are each conjugated to a polymerase. The polymerase embedded in the nanopores are exposed to a polynucleotide template and a plurality of nucleotides, each comprising an oligonucleotide tag. When the tagged nucleotides complementary to the polynucleotide template is captured by the polymerase active site, the tag moiety becomes positioned in the nanopore. A potential is applied and the presence of the tag in the pore causes a distinctive blocking current compared to the open pore current. The blocking currents are measured as the polymerase synthesizes the strand complementary to the polynucleotide template. The sequences of the measured blocking current are used to identify the sequence of polynucleotide template.

After the polynucleotides in the ternary complexes are sequenced, the sequencing chip is washed, and the ternary complexes are removed from the sequencing chip according to the general method of Example 1. The sequencing chip is then prepared for reuse and are reloaded with a new ternary complex library.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for polynucleotide sequencing comprising:
- contacting a plurality of polynucleotides with at least one primer and at least one polymerase to form a plurality of ternary complexes;
- binding the plurality of ternary complexes to a surface comprising a plurality of loci, wherein each ternary complex is bound to a single locus of the surface, and wherein the binding includes binding the at least one polymerase to the surface;
- detecting one or more bases of the plurality of polynucleotides, wherein detection occurs when the plurality of ternary complexes are bound to the surface;
- removing the plurality of ternary complexes from the surface; and
- repeating the contacting, binding, detecting, and removing steps to sequence the plurality of polynucleotides.

2. The method of claim 1, wherein removing the plurality of ternary complexes from the surface comprises washing the surface.

3. The method of claim 2, wherein washing the surface comprises contacting the surface with one or more of a solvent, heat, a small molecule, a nucleic acid, or a protein.

4. The method of claim 3, wherein washing the surface comprises contacting the surface with a small molecule, and the small molecule comprises a first moiety configured for conjugation to a second moiety.

5. The method of claim 3, wherein washing the surface comprises contacting the surface with a solvent, and the solvent comprises an organic solvent.

6. The method of claim 3, wherein washing the surface comprises contacting the surface with a protein, and the protein comprises a proteinase or nuclease.

7. The method of claim 1, wherein the contacting, binding, detecting, and removing steps are repeated at least three times.

8. The method of claim 1, wherein detecting one or more bases of the plurality of polynucleotide comprises contacting each ternary complex of the plurality of ternary complexes with a nucleotide comprising a label.

9. The method of claim 1, wherein the plurality of polynucleotides includes at least 100,000 unique polynucleotides, and wherein each unique polynucleotide comprises a different nucleic acid sequence from every other unique polynucleotide in the plurality of polynucleotides.

10. The method of claim 1, wherein each polynucleotide of the plurality of polynucleotides comprises 50 bases to 30,000 bases.

11. A method for sequencing a sample polynucleotide, the method comprising:
- binding a polymerase to a solid support;
- forming a ternary complex by contacting a sample polynucleotide with a primer and the polymerase;
- detecting a base of the sample polynucleotide when the ternary complex is bound to a solid support, wherein detecting comprises contacting the ternary complex with a nucleotide comprising a label; and
- washing the solid support to remove the ternary complex from the solid support.

12. The method of claim 11, wherein the solid support comprises a binding moiety configured to bind the ternary complex.

13. The method of claim 12, wherein the binding moiety comprises biotin.

14. The method of claim 12, wherein the binding moiety comprises a first biotin, the polymerase of the ternary complex comprises a second biotin, and the first biotin and the second biotin are conjugated via a streptavidin.

15. The method of claim 11, wherein the label is a luminescent label.

16. The method of claim 11, wherein detecting further comprises excitation with a laser.

17. The method of claim 11, wherein, prior to forming the ternary complex, the sample polynucleotide is attached to the solid support.

18. The method of claim 11, wherein detecting the base of the sample polynucleotide comprises measuring a change in current or voltage.

19. The method of claim 11, further comprising repeating the binding, forming, detecting, and washing steps to sequence the sample polynucleotide.

* * * * *